United States Patent
Patti et al.

(10) Patent No.: US 7,045,131 B2
(45) Date of Patent: *May 16, 2006

(54) STAPHYLOCOCCAL IMMUNOTHERAPEUTICS VIA DONOR SELECTION AND DONOR STIMULATION

(75) Inventors: Joseph M. Patti, Cumming, GA (US); Timothy J. Foster, Dublin (IR); Magnus Hook, Houston, TX (US)

(73) Assignee: Inhibitex, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/091,494

(22) Filed: Mar. 7, 2002

(65) Prior Publication Data

US 2002/0159997 A1  Oct. 31, 2002

Related U.S. Application Data

(62) Division of application No. 09/386,980, filed on Aug. 31, 1999, now Pat. No. 6,692,739.

(60) Provisional application No. 60/098,449, filed on Aug. 31, 1998.

(51) Int. Cl.
*A61K 39/085* (2006.01)

(52) U.S. Cl. .............. 424/165.1; 424/164.1; 424/142.1; 424/130.1; 530/350; 530/387.1

(58) Field of Classification Search .......... 536/23.7; 530/350, 388.2, 388.4, 389.1, 389.5, 388.3, 530/388.15, 387.5, 387.1; 424/164.1, 150.1, 424/169.1, 165.1, 184.1, 130.1, 137.1, 234.1, 424/185.1, 142.1; 435/7.1, 7.32
See application file for complete search history.

(56) References Cited

U.S. PATENT DOCUMENTS

| | | | |
|---|---|---|---|
| 4,245,039 A * | 1/1981 | Heimburger et al. | 435/13 |
| 4,312,942 A * | 1/1982 | Blobel et al. | 435/7 |
| 4,318,902 A | 3/1982 | Stephan | |
| 4,732,757 A | 3/1988 | Stolle et al. | |
| 4,965,068 A | 10/1990 | Stephan et al. | |
| 5,034,515 A | 7/1991 | Proctor | |
| 5,055,455 A * | 10/1991 | Pier | 514/54 |
| 5,292,513 A | 3/1994 | Gristina et al. | |
| 5,496,706 A * | 3/1996 | Kuusela et al. | 435/7.33 |
| 5,505,945 A | 4/1996 | Gristina et al. | |
| 5,530,102 A | 6/1996 | Gristina et al. | |
| 5,571,511 A | 11/1996 | Fischer | |
| 5,585,106 A | 12/1996 | Gristina et al. | |
| 5,591,441 A | 1/1997 | Gristina et al. | |
| 5,648,240 A * | 7/1997 | Hook et al. | 435/69.3 |
| 5,681,565 A | 10/1997 | Gristina et al. | |
| 5,707,627 A * | 1/1998 | Gristina et al. | |
| 5,718,899 A * | 2/1998 | Gristina et al. | |
| 5,770,208 A | 6/1998 | Fattom et al. | |
| 5,770,234 A | 6/1998 | Gristina et al. | |
| 5,776,712 A * | 7/1998 | Kuusela et al. | 435/7.33 |
| 5,817,312 A | 10/1998 | Gristina et al. | |
| 5,955,074 A | 9/1999 | Fischer | |
| 5,955,078 A * | 9/1999 | Burnham et al. | 424/190.1 |
| 5,980,910 A | 11/1999 | Pier | |
| 6,008,341 A * | 12/1999 | Foster et al. | 536/23.7 |
| 6,077,677 A * | 6/2000 | Hodgson et al. | 435/7.1 |
| 6,177,084 B1* | 1/2001 | Foster et al. | 424/243.1 |
| 6,221,397 B1 | 4/2001 | Russell-Jones et al. | |
| 6,274,144 B1 | 8/2001 | Wang et al. | |
| 6,288,214 B1* | 9/2001 | Hook et al. | 530/387.1 |
| 6,299,879 B1* | 10/2001 | Boden Wastfalt et al. | 424/185.1 |
| 6,685,943 B1* | 2/2004 | Hook et al. | 424/185.1 |
| 6,692,739 B1* | 2/2004 | Patti et al. | 424/130.1 |
| 6,733,758 B1* | 5/2004 | Guss et al. | 424/243.1 |
| 2003/0006209 A1* | 1/2003 | Stefen et al. | 215/386 |
| 2003/0099656 A1* | 5/2003 | Patti et al. | 424/165.1 |
| 2004/0038327 A1* | 2/2004 | Foster et al. | 435/7.32 |
| 2004/0142348 A1* | 7/2004 | Foster et al. | 435/6 |

FOREIGN PATENT DOCUMENTS

| | | | |
|---|---|---|---|
| WO | 85/05553 | * | 12/1985 |
| WO | WO 93/09811 | | 5/1993 |
| WO | WO 93/17044 | | 9/1993 |

| WO | WO 94/06830 |   | 3/1994 |
| --- | --- | --- | --- |
| WO |    94/13310 | * | 6/1994 |
| WO |    94/18327 | * | 8/1994 |
| WO | WO 95/34655 |   | 12/1995 |
| WO | WO 97/43314 |   | 11/1997 |
| WO | WO 97/48727 |   | 12/1997 |
| WO | WO 98/31389 |   | 7/1998 |
| WO | WO 98/38312 |   | 9/1998 |
| WO | WO 99/27109 |   | 6/1999 |
| WO | WO 00/12131 |   | 3/2000 |

OTHER PUBLICATIONS

Annaix, V et al, FEMS microbiology immunology, Oct. 1990, vol. 2(3), pp. 147-153, Structures involved in teh binding of humn fibrinogen to Candida albicans germ tubes (abstract only).*
Nagata, H et al, Journal of Osaka University Dental School, Dec. 1994, vol. 34, pp. 37-44, Characterization of coaggregation and fibrinogen binding by Porphyromonas gingivalis. (abstract only).*
Fischer, G, Pediatric Clinics of North America, vol. 35(3), Jun. 1988, pp 517-533, Therapeutic uses of intravenous gammaglobulin for Pediatric Infections.*
Wadstrom, ACTA Microbiologica Hungarica, vol. 38, 1991, Microbial Adhesion: New concepts for development, pp 164-165.*
Nilsson et al, J. Clin. Invest., Vaccination with a recombinant fragment of collagen adhesin provides protection against *Staphylococcus aureus* mediated septic death.*
Boden et al, Infection and Immunity, vol. 57(8), pp. 2358-2363, Aug. 1989.*
Harris, LG et al, European Cells and Material, vol. 4, 2002, pp. 39-60.*
Nilsson, M et al, Infection and Immunity, vol. 66(6), pges 2666-2673, Jun. 1998, A Fibriogen binding protein of *Staphylococcus epidermidis*.*
Christensen, GD et al, Infection and Immunity, vol. 40(1), pp. 407-410, Apr. 1983.*
Neonatal Infectious Diseases, Program Issue APS-SPR, Washington DC, May 1-4, 1989, vol. 25, No. 4, Part 2.
Agarwal, "Subcutaneous Staphylococcal Infection in Mice . . . ", Br. J. Exp. Pathology, Oct. 1967, vol. 48(5), p. 483-500.
Fischer, "Therapeutic Uses of Intravenous Gammaglobulin for Pediatric Infections", Pediatric Clinics of North America, vol. 35, No. 3, Jun. 1988, pp. 517-533.
McDevitt et al., "Identification of the ligand-binding domain of the surface-located . . . " Molecular Microbiology (1995), 16(5), pp. 895-907.
Murazyan et al., "Staphyloccal Infections and Their Treatment In Burned Patients", ACTA Chirurgiae Plasticae 24, 3, 1982, pp. 180-184.
Fattom et al., "A *Staphylococcus aureus* Capsular Polysaccharide (CP) Vaccine and CP-Specific . . . ", Infection and Immunity, May 1996, vol. 1996, vol. 64, No. 5, pp. 1659-1665.
Nilsson et al., "Vaccination with a Recombinant Fragment of Collagen Adhesin Provides Protection . . . ", J. Clin. Invest., vol. 101, No. 12, Jun. 1998, pp. 2640-2649.
Patti et al., "Identification and Biochemical Characterization of the Ligand Binding Domain . . . ", Biochemistry 1993, 32, pp. 11428-11435.
Yoshida et al., "Induction of Resistance with Heat-Killed Compact-type Strains of *Staphylococcus aureus* . . . " Infection and Immunity, Nov. 1975, vol. 12, No. 5, pp. 939-942.

Wadstrom, "Microbial adhesion: new concepts for development . . . ", Acta Microbiologica Hungarica 38, 1991, pp. 164-165.
Takeda et al., "Protection Against Endocarditis Due to *Staphylococcus epidermidis* . . . ", Circulation, vol. 84, No. 6, Dec. 1991, pp. 2539-2546.
Smeltzer et al., "Prevalence and chromosomal map location . . . ", Gene 196 (1997), pp. 249-259.
Martinez et al., "Heterogeneous Surface Distribution of the Fibrinogen-Binding Protein . . . ", Infection and Immunity, Feb. 1994, vol. 62, No. 2, pp. 709-712.
Espersen et al., "Immunization of Mice with the Fibronectin-Binding Protein . . . ", Acta path. microbiol. immunol. scand. Sect. C, 93: 53-58, 1985.
Nilsson et al., "Vaccination with a Recombinant Fragment of Collagen Adhesin Provides . . . ", J. Clin. Invest., vol. 101, No. 12, Jun. 1998, pp. 2640-2649.
McDevitt et al., "Variation in the size of the repeat region of the fibrinogen receptor", Microbiology, 1995, 141, 937-943.
McCrea et al., "The serine-aspartate repeat (Sdr) protein family . . . ", Microbiology (2000), 146, pp. 1535-1546.
Hartford et al., "The dipeptide repeat region of the fibrinogen-binding protein (clumping factor) is required . . . ", Molecular Microbiology (1997), 25(6), pp. 1065-1076.
Foster et al., "Surface-associated proteins of *Staphylococcus aureus*: Their possible roles in virulence", FEMS Microbiology Letters 118 (1994), pp. 199-206.

* cited by examiner

*Primary Examiner*—Lynette R. F. Smith
*Assistant Examiner*—Ginny Allen Portner
(74) *Attorney, Agent, or Firm*—B. Aaron Schulman; Stites & Harbison PLLC

(57) ABSTRACT

A method and composition for the passive immunization of patients infected with or susceptible to infection from *Staphylococcus* bacteria such as *S. aureus* and *S. epidermidis* infection is provided that includes the selection or preparation of a donor plasma pool with high antibody titers to carefully selected *Staphylococcus* adhesins or MSCRAMMs, or fragments or components thereof, or sequences with substantial homology thereto. The donor plasma pool can be prepared by combining individual blood or blood component samples which have higher than normal titers of antibodies to one or more of the selected adhesins or other proteins that bind to extracellular matrix proteins, or by administering carefully selected proteins or peptides to a host to induce the expression of desired antibodies, and subsequently recovering the enhanced high titer serum or plasma pool from the treated host. In either case, the donor plasma pool is preferably purified and concentrated prior to intravenous introduction into the patient, and the present invention is advantageous in that a patient can be immunized against a wide variety of potentially dangerous staphylococcal infections. Kits for identifying potential donor with high titers of the selected adhesins are also provided. The present invention thus provides methods and compositions which can be highly effective against infections associated with *Staphylococcus* bacteria.

12 Claims, 2 Drawing Sheets

STAPHYLOCOCCAL IMMUNOTHERAPEUTICS VIA DONOR SELECTION AND DONOR STIMULATION

Figure 1:
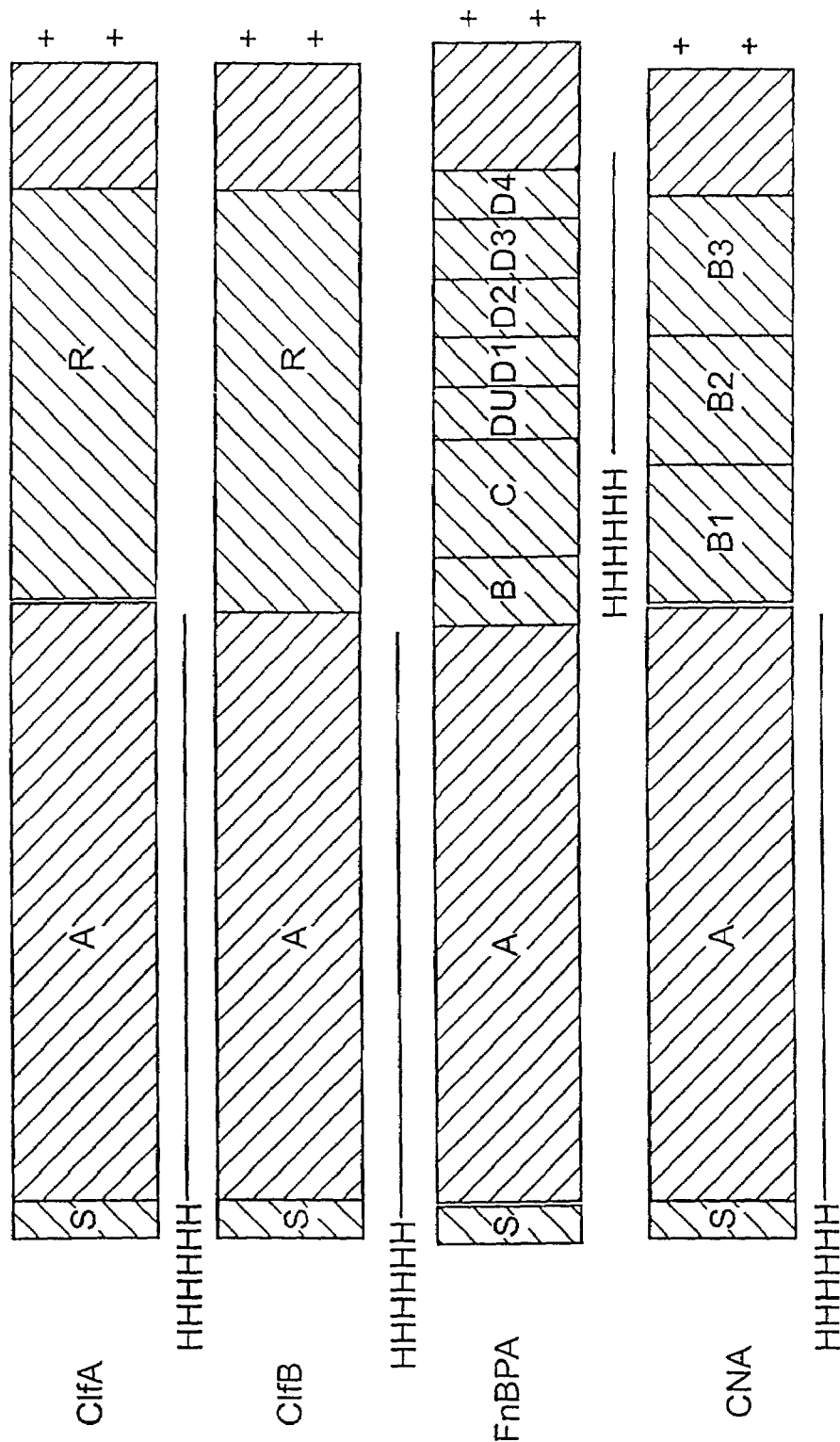

This application is a divisional application of U.S. Ser. No. 09/386,980, filed Aug. 31, 1999 now U.S. Pat. No. 6,692,739, which claims the benefit of U.S. provisional application Ser. No. 60/098,449, filed Aug. 31, 1998.

The invention is in the field of biological products for the treatment, prevention and diagnosis of bacterial infections.

BACKGROUND OF THE INVENTION

The staphylococci are Gram-positive spherical cells, usually arranged in grape-like irregular clusters. Some are members of the normal flora of the skin and mucous membranes of humans, others cause suppuration, abscess formation, a variety of pyogenic infections, and even fatal septicemia. Pathogenic staphylococci often hemolyze blood, coagulate plasma, and produce a variety of extracellular enzymes and toxins. The most common type of food poisoning is caused by a heat-stable staphylococci enterotoxin.

The genus *Staphylococcus* has at least 30 species. Three main species of clinical importance are *Staphylococcus aureus*, *Staphylococcus epidermidis*, and *Staphylococcus haemolyticus*. *Staphylococcus aureus* is coagulase-positive, which differentiates it from the other species. *S. aureus* is a major pathogen for humans. Almost every person has some type of *S. aureus* infection during a lifetime, ranging in severity from food poisoning or minor skin infections to severe life-threatening infections. The coagulase-negative staphylococci are normal human flora which sometimes cause infection, often associated with implanted devices, especially in very young, old and immunocompromised patients. Approximately 75% of the infections caused by coagulase-negative staphylococci are due to parasitic *S. epidermidis*. Infections due to *Staphylococcus haemolyticus*, *Staphylococcus hominis*, and other species are less common. *S. saprophyticus* is a relatively common cause of urinary tract infections in young women.

*Staphylococcus* bacteria such as *S. aureus* thus cause a spectrum of infections that range from cutaneous lesions such as wound infections, impetigo, and furuncles to life-threatening conditions that include pneumonia, septic arthritis, sepsis, endocarditis, and biomaterial related infections. *S. aureus* colonization of the articular cartilage, of which collagen is a major component, within the joint space appears to be an important factor contributing to the development of septic arthritis. Hematogenously acquired bacterial arthritis remains a serious medical problem. This rapidly progressive and highly destructive joint disease is difficult to eradicate. Typically less than 50% of the infected patients failing to recover without serious joint damage. *S. aureus* is the predominant pathogen isolated from adult patients with hematogenous and secondary osteomyelitis.

In hospitalized patients, *Staphylococcus aureus* is a major cause of infection. Initial localized infections of wounds or indwelling medical devices can lead to more serious invasive infections such as septicemia, osteomyelitis, mastitis and endocarditis. In infections associated with medical devices, plastic and metal surfaces become coated with host plasma and matrix proteins such as fibrinogen and fibronectin shortly after implantation. The ability of *Staphylococcus* bacteria such as *S. aureus* to adhere to these proteins is essential to the initiation of infection. Vascular grafts, intravenous catheters, artificial heart valves, and cardiac assist devices are thrombogenic and prone to bacterial colonization. *S. aureus* is the most damaging pathogen of such infections, and other Staphylococci bacteria such as *S. epidermidis* are also responsible for a significant amount of dangerous infections, particularly those associated with implanted devices.

There is a strong and rapidly growing need for therapeutics to treat infections from *Staphylococcus* bacteria such as *S. aureus* and *S. epidermidis* infections which are effective against antibiotic resistant strains of the bacteria. The U.S. National Institutes for Health has recently indicated that this goal is now a national priority.

MSCRAMMs

The successful colonization of the host is a process required for most microorganisms to cause infections in animals and humans. Microbial adhesion is the first crucial step in a series of events that can eventually lead to disease. Pathogenic microorganisms colonize the host by attaching to host tissues or serum conditioned implanted biomaterials, such as catheters, artificial joints, and vascular grafts, through specific adhesins present on the surface of the bacteria. MSCRAMMs (Microbial Surface Components Recognizing Adhesive Matrix Molecules) are a family of cell surface adhesins that recognize and specifically bind to distinct components in the host's extracellular matrix. Once the bacteria have successfully adhered to and colonized host tissues, their physiology is dramatically altered and damaging components such as toxins and proteolytic enzymes are secreted. Moreover, adherent bacteria often produce a biofilm and quickly become more resistant to the killing effect of most antibiotics.

For example, *S. aureus* is known to express a repertoire of different MSCRAMMs that can act individually or in concert to facilitate microbial adhesion to specific host tissue components. MSCRAMMs provide an excellent target for immunological attack by antibodies. The presence of the appropriate anti-MSCRAMM high affinity antibodies has a double-edged attack, first the antibodies prevent microbial adherence and second the increased titers of MSCRAMM antibodies facilitate a rapid clearance of the organism from the body through bacterial lysis, opsonization, phagocytosis and complement activation.

Passive Immunization to Bacterial Infections

Immunoglobulins (A, D, E, G, and M) are used by the body as a primary defense to infections. Complement, available as a precursor protein which is activated by the presence of microorganisms and globulins, also exhibits antibacterial activities. After previous antigenic exposure, the immune system produces a series of globulins which attach to and coat bacteria or neutralize viruses so that they are readily recognized, phagocytized and destroyed by neutrophils and macrophages. Foreign proteins of invading organisms also stimulate a humoral immune response which over a period of time from three to six weeks amplifies the number of cells designed to recognize and destroy specific invaders.

In the last decade, intravenous immunoglobulin (IVIG) therapy has become a major treatment regime for bacterial infections, especially in immunocompromised patients (Siber, *New Eng. J. Med.*, 327:269–271, 1992). IVIG therapy has exhibited efficacy against more than thirty-five diseases caused by immunopathologic mechanisms. Passive immunization against infections has been particularly successful with immune globulins specific for tetanus, hepatitis B, rabies, chicken pox and cytomegalovirus. There has been an inconsistent and disappointing response to the use of immunoglobulins to prevent nosocomial infections, likely due to the variety of strains of bacteria found in hospitals and the emergence of new serotypes. Passive immunization requires the presence of high and consistent titers of antibodies to the infecting pathogens.

Supplemental immunoglobulin therapy has been shown to provide some measure of protection against certain encapsulated bacteria such as *Hemophilus infuenzae* and *Streptococcus pneumoniae*. Infants who are deficient in antibody are susceptible to infections from these bacteria and bacteremia and sepsis are common. When anti-Streptococcal and anti-Hemophilus antibodies are present, they provide protection by promoting clearance of the respective bacteria from the blood. In the case of antibody to *Staphylococcus*, the potential use of supplemental immunoglobulin to prevent or treat infection has been much less clear.

Early attempts to treat *Staphylococcus* infections focused on the potential use of supplemental immunoglobulin to boost peritoneal defenses, such as opsonic activity, in patients receiving continuous ambulatory peritoneal dialysis. Standard intravenous immunoglobulin (IVIG) was shown to have lot to lot variability for opsonic activity to *S. epidermidis* (L. A. Clark and C. S. F. Easmon, *J. Clin. Pathol.* 39:856 (1986)). In this study, one third of the IVIG lots tested had poor opsonization with complement, and only two of fourteen were opsonic without complement. Thus, despite the fact that the IVIG lots were made from large plasma donor pools, good opsonic antibody to *S. epidermidis* was not uniformly present. Moreover, this study did not examine whether IVIG could be used to prevent or treat *S. epidermidis* infections or bacterial sepsis.

Prior studies have associated coagulase-negative *Staphylococcus* bacteria, such as *S. epidermidis*, as the most common species causing bacteremia in neonates receiving lipid emulsion infusion (Freeman, J. et al., *N. Engl. J. Med.* 323:301, 1990). These neonates had low levels of opsonic antibody to *S. epidermidis* despite the fact that the sera had clearly detectable levels of IgG antibodies to *S. epidermidis* peptidoglycan (Fleer, A. et al., *J. Infect. Dis.* 2:426, 1985). This was surprising because anti-peptidoglycan antibodies were presumed to be the principal opsonic antibodies. Thus, while suggesting that neonatal susceptibility to *S. epidermidis* might be related to impaired opsonic activity, these studies also suggested that many antibodies directed against *S. epidermidis* are not opsonic and would not be capable of providing protection when given passively to neonates.

In addition, an antigen binding assay was used to analyze IgG antibody to *S. epidermidis* in patients with uncomplicated bacteremia and those with bacteremia and endocarditis (F. Espersen et al., *Arch. Intern. Med.* 147:689 (1987)). This assay used an ultrasonic extract of *S. epidermidis* to identify *S. epidermidis* specific IgG. None of the patients with uncomplicated bacteremia had IgG antibodies to *S. epidermidis*. These data suggest that IgG does not provide effective eradication of *S. epidermidis* from the blood. In addition, 89% of bacteremic patients with endocarditis developed high levels of IgG to *S. epidermidis*. In these patients, IgG was not protective since high levels of IgG antibody were associated with serious bacteremia and endocarditis. Based on these studies, the protective role of IgG in *S. epidermidis* sepsis and endocarditis was questionable, especially in the presence of immaturity, debilitation, intralipid infusion, or immunosuppression.

Animal studies in the literature that demonstrated immunoglobulin protection against *Staphylococcus* infections have shown strain specificity by enzyme-linked immunosorbent assays (ELISA) and have utilized normal adult mice in protection studies. Animal models typically have used mature animals with normal immunity with unusually virulent strains or overwhelming-challenge doses of bacteria. Human patients are generally immunologically immature or debilitated. Human patients also get somewhat indolent infections with low virulence pathogens such as *S. epidermidis* with death usually attributable to secondary complications. Models that have used unusual strains or overwhelming bacterial doses, generally induce rapid fulminant death. These are important factors since antibodies generally work in concert with the host cellular immune system (neutrophils, monocytes, macrophages and fixed reticuloendothelial system). The effectiveness of antibody therapy may therefore be dependent on the functional immunologic capabilities of the host. To be predictive, animal models must closely emulate the clinical condition in which the infection would occur and capture the setting for therapy. Moreover, the animal studies have yielded inconsistent results.

One model has been reported which used an unusually virulent strain of *S. epidermidis*. Infected-mature mice developed 90 to 100% mortality within 24 to 48 hours (K. Yoshida et al., *Japan. J. Microbiol.* 20:209 (1976)). Antibody to *S. epidermidis* surface polysaccharide was protective in these mice. Protection was shown to occur with an IgM fraction, but not the IgG fraction (K. Yoshida and Y. Ichiman, *J. Med. Microbiol* 11:371 (1977)). This model, however, presents a pathology which is very different from that seen in typically infected patients. Intraperitoneally-challenged mice developed symptoms of sepsis within minutes of receiving the injection and died in 24 to 48 hours. This particular pathology is not observed in *Staphylococcus* infected humans. The highly virulent strain of *S. epidermidis* may represent an atypical type of infection. moreover, isolates of *S. epidermidis* from infected humans did not kill mice in this model.

In 1987, these animal studies were extended to include the evaluation of antibodies in human serum against selected virulent strains of *S. epidermidis* (Y. Ichiman et al., *J. Appl. Bacteriol.* 63:165 (1987)). In contrast to the previous data, protective antibody was found in the IgA, IgM and IgG immunoglobulin fractions. A definitive role for any single class of immunoglobulin (IgG, IgM, IgA) could not be established.

In this animal model, normal adult mice were used and mortality was determined. Death was considered to be related to the effect of specific bacterial toxins, not sepsis (K. Yoshida et al., *Japan J. Microbiol.* 20:209 (1976)). Most clinical isolates did not cause lethal infections, and quantitative blood cultures were not done. Moreover, this study provided little insight as to whether antibody could successfully prevent or treat *S. epidermidis* sepsis in immature or immunosuppressed patients.

In a later study, serotype specific antibodies directed against *S. epidermidis* capsular polysaccharides were tested in the animal model. Results showed that serotype-specific antibodies were protective, but that each antibody was directed against one serotype as measured by ELISA. Protection was equally serotype specific. Protection against heterologous strains did not occur. In addition, it was concluded that protection was afforded by the IgM antibody.

There has been no compelling evidence that IVIG would be effective to treat *S. epidermidis* infections or sepsis, particularly where the patients are immature or immune suppressed or where multiple *S. epidermidis* serotypes are involved. Thus, for example, a recent and extensive review of the pathogenesis, diagnosis, and treatment of *S. epidermidis* infections does not include immunoglobulin as a potential prophylactic or therapeutic agent (C. C. Patrick, *J. Pediatr.* 116:497 (1990)). In addition, there have been no U.S. patents which describe the effective use of IVIG therapy in conjunction with antibodies to MSCRAMMs such as described above.

U.S. Pat. No. 5,505,945 discloses compositions for passive immunity that contain a full repertoire of immunoglobulins, including IgA, IgM, and IgG to combat infections from microorganisms and viruses at wound, surgical, or burn sites. The compositions contain elevated antibody titers for several pathogens, including *S. aureus*, Coagulase Negative *Staphylococci Enterococci, S. epidermidis, P. aeruginose, E. coli*, and Enterobacter spp. However, these compositions are specifically designed to avoid the use of intravenous immunoglobulin or IVIG therapy, and instead are applied in the form of ointments, creams, sprays and the like which are designed for topical application only.

U.S. Pat. No. 4,717,766 discloses a method of preparing high titer anti-respiratory syncytial virus intravenous immunoglobulins.

U.S. Pat. No. 5,219,578 describes a composition and method for immunostimulation in mammals, and specifically describes the isolation of an IgG fraction from goats free from foreign or artificially induced antigens and the utilization of the isolated immunoglobulins fraction to induce a stimulated immune response.

U.S. Pat. No. 5,548,066 describes a method for drawing blood from a donor animal, permitting blood to clot, separating liquid from cellular material, and then clarifying, concentrating and sterilizing the product.

U.S. Pat. No. 4,412,990 discloses an intravenous pharmaceutical composition containing immunoglobulin (IgG) and fibronectin that exhibits a synergistic opsonic activity which results in enhanced phagocytosis of bacteria, immune complexes and viruses.

U.S. Pat. No. 4,994,269 discloses the topical use of monoclonal antibodies for the prevention and treatment of experimental *P. aeruginosa* lung infections. Specifically, the antibodies are administered via aerosol spray to the lungs. Results show beneficial effects in the treatment of affected patients.

U.S. Pat. No. 4,714,612 discloses the use of a non-specific gamma globulin IgG in a mouthwash for the prevention of gingivitis. Another mouthwash with monoclonal antibodies is described by Ma et al. in *Arch. Oral Biol.,* 35 Supp: 115S–122S, in 1990. The monoclonal antibodies were specific for *Streptococcus mutans*, and patients treated with the mouthwash remained free of *S. mutans* for up to two years. Those who did not take the mouthwash experiences recolonization of *S. mutans* within two days.

U.S. Pat. Nos. 5,718,889 and 5,505,945 describe the direct, concentrated local delivery of passive immunity which is accomplished by applying a composition having a full repertoire of immunoglobulins (IgG, IgM and IgA) to biomaterials, implants, tissues, and wound and burn sites.

U.S. Pat. No. 5,571,511 describes the use of immunoglobulin from individual samples or pools of serum, plasma, whole blood, or tissue for the treatment of a *Staphylococcus* infection. Immunoglobulin is identified by performing a first assay to identify immunoglobulin which is reactive with a preparation of a first *Staphylococcus* organism, performing a second assay to identify immunoglobulin which is reactive with a preparation of a second *Staphylococcus* organism, and selecting immunoglobulin which is reactive with the preparations from both the first and second *Staphylococcus* organisms. Reactivity is determined in immunological assays which may be binding assays, opsonization assays, or clearance assays. Preferably, the preparations of the first and the second *Staphylococcus* organisms are derived from different serotypes or different species, such as *S. epidermidis* and *S. aureus*, and more preferably, the first preparation is from *S. epidermidis* (Hay, ATCC 55133).

U.S. Pat. No. 5,412,077 describes the screening of plasma samples for effective antibody titers for the treatment or prophylaxis of an infection caused by a respiratory virus.

Accordingly, there still remains a need to provide more effective products and methods which make use of antibodies against MSCRAMMs and can be utilized in methods of intravenous immunoglobulin therapy so as to prevent and/or treat *Staphylococcus* infections, and preferably those that can exhibit a broad spectrum immunization against various strains of *Staphylococcus* bacteria.

Active Immunization to Bacterial Infections

Historically, studies on bacterial adherence have focused primarily on Gram-negative bacteria, which express a wide variety of adhesive proteins on their cell surface (Falkow, S., et al., *Cell,* 65:1099–1102, 1992). These adhesins recognize specific glycoconjugates exposed on the surface of host cells (particularly epithelial layers). Employing the lectin-like structures in attachment allows the microorganism to efficiently colonize the epithelial surfaces. This provides the bacteria an excellent location for replication and also the opportunity to disseminate to neighboring host tissues. It has been demonstrated that immunization with pilus adhesins can elicit protection against microbial challenge, such as in *Hemophilus influenza* induced otitis media in a chinchilla model (Sirakova et al., *Infect. Immun,* 62(5):2002–2020, 1994), *Moraxella bovis* in experimentally induced infectious bovine keratoconjunctivitis (Lepper et al., *Vet Microbiol,* 45(2–3):129–138, 1995), and *E. coli* induced diarrhea in rabbits (McQueen et al., *Vaccine,* 11:201–206, 1993). In most cases, immunization with adhesins leads to the production of immune antibodies that prevent infection by inhibiting bacterial attachment and colonization, as well as enhancing bacterial opsonophagocytosis and antibody-dependent complement-mediated killing.

The use of molecules that mediate the adhesion of pathogenic microbes to host tissue components as vaccine components is emerging as a critical step in the development of future vaccines. Because bacterial adherence is the critical first step in the development of most infections, it is an attractive target for the development of novel vaccines. An increased understanding of the interactions between MSCRAMMs and host tissue components at the molecular level coupled with new techniques in recombinant DNA technology have laid the foundation for a new generation of subunit vaccines. Entire or specific domains of MSCRAMMs, either in their native or site-specifically altered forms, can now be produced. Moreover, the ability to mix and match MSCRAMMs from different microorganisms creates the possibility of designing a single vaccine that will protect against multiple bacteria.

The recent clinical trials with a new subunit vaccine against whooping cough, consisting of the purified *Bordatella pertussis* MSCRAMMs filamentous hemagglutinin and pertactin, in addition to an inactivated pertussis toxin, are a prime example of the success of this type of approach. Several versions of the new acellular vaccine were shown to be safe and more efficacious than the old vaccine that contained whole bacterial cells (Greco et al., *N Eng J Med*, 334:341–348, 1996; Gustaffson et al., *N Eng J Med*, 334: 349–355, 1996).

Natural immunity to *Staphylococcus* infections remains poorly understood. Typically, healthy humans and animals exhibit a high degree of innate resistance to *Staphylococcus* bacteria such as *S. aureus*. Protection is attributed to intact epithelial and mucosal barriers and normal cellular and humoral responses. Titers of antibodies to *S. aureus* components are elevated after severe infections (Ryding et al., *J. Med Microbiol*, 43(5):328–334, 1995), however to date there is no serological evidence of a correlation between antibody titers and human immunity.

Over the past several decades live, heat-killed, and formalin fixed preparations of *S. aureus* cells have been tested as vaccines to prevent staphylococcal infections. A multicenter clinical trial was designed to study the effects of a commercial vaccine, consisting of a staphylococcus toxoid and whole killed staphylococci, on the incidence of peritonitis, exit site infection, and *S. aureus* nasal carriage among continuous peritoneal dialysis patients (Poole-Warren, L. A., et al., *Clin Nephrol*, 35:198–206, 1991). Although immunization with the vaccine elicited an increase in the level of specific antibodies to *S. aureus*, the incidence of peritonitis was unaffected. Similarly, immunization of rabbits with whole cells of *S. aureus* could not prevent or modify any stage in the development of experimental endocarditis, reduce the incidence of renal abscess, or lower the bacterial load in infected kidneys (Greenberg, D. P., et al., *Infect Immun*, 55:3030–3034, 1987).

Currently there is no FDA approved vaccine for the prevention of *S. aureus* infections. However, a *S. aureus* vaccine (StaphVAX), based on the capsular polysaccharide, is currently being developed by NABI (North American Biologicals Inc.). This vaccine consists of type 5 or type 8 capsular polysaccharides conjugated to *Pseudomonas aeruginosa* exotoxin A (rEPA). The vaccine is designed to induce type-specific opsonic antibodies and enhance opsonophagocytosis (Karakawa, W. W., et al., *Infect Immun*, 56:1090–1095, 1988). Using a refined lethal challenge mouse model (Fattom, A., et al., *Infect Immun*, 61:1023–1032, 1996) it has been shown that intraperitoneal infusion of type 5 specific IgG reduces the mortality of mice inoculated intraperitoneally with *S. aureus*. The type 5 capsular polysaccharide-rEPA vaccine has also been used to vaccinate seventeen patients with end-stage renal disease (Welch, et al., *J Amer Soc Nephrol*, 7(2):247–253, 1996). Geometric mean (GM) IgG antibody levels to the type 5 conjugate increased between 13 and 17-fold after the first immunization, however no additional increases could be detected after additional injections. Moreover, these vaccination regimens were not able to treat a variety of bacterial strains.

Interestingly, the GM IgM levels of the vaccinated patients were significantly lower than control individuals. Supported by the animal studies, the vaccine has recently completed a Phase II trial in continuous ambulatory peritoneal dialysis patients. The clinical trial showed the vaccine to be safe but ineffective in preventing staphylococcal infections (NABI SEC FORM 10-K405, Dec. 31, 1995). Two possible explanations for the inability of StaphVAX to prevent infections related to peritoneal dialysis in vaccinated patients are that the immunogenicity of the vaccine was too low due to suboptimal vaccine dosing or that antibodies in the bloodstream are unable to affect infection in certain anatomic areas, such as the peritoneum.

Incidence of gram-positive bacteria related sepsis is increasing. In fact between one-third and one-half of all cases of sepsis are caused by gram-positive bacteria, particularly *S. aureus* and *S. epidermidis*. In the United States, it can be estimated that over 200,000 patients will develop gram-positive related sepsis this year. Using a mouse model (Bremell, et al., *Infect Immun*, 59(8):2615–2623, 1991), it has been clearly demonstrated in PCT WO 97/43314 that active immunization with M55 domain of the Col-binding MSCRAMM can protect mice against sepsis induced death. Mice were immunized subcutaneously with either M55 or a control antigen (bovine serum albumin) and then challenged intravenously with *S. aureus*. Eighty-three percent (35/42) of the mice immunized with M55 survived compared to only 27% of the BSA immunized mice (12/45). This a compilation of three separate studies.

Schennings et al. demonstrated that immunization with fibronectin binding protein from *S. aureus* protects against experimental endocarditis in rats (*Micro Pathog*, 15:227–236, 1993). Rats were immunized with a fusion protein (gal-FnBP) encompassing beta-galactosidase and the domains of fibronectin binding protein from *S. aureus* responsible for binding to fibronectin. Antibodies against gal-FnBP were shown to block the binding of *S. aureus* to immobilized fibronectin in vitro. Endocarditis in immunized and non-immunized control rats was induced by catheterization via the right carotid artery, resulting in damaged aortic heart valves which became covered by fibrinogen and fibronectin. The catheterized rats were then infected intravenously with $1 \times 10^5$ cells of *S. aureus*. The number of bacteria associated with aortic valves was determined 1½ days after the challenge infection and a significant difference in bacterial numbers between immunized and non-immunized groups was then observed.

A mouse mastitis model was used by Mamo, et al., in 1994 (*Vaccine*, 12:988–992) to study the effect of vaccination with fibrinogen binding proteins (especially FnBP-A) and collagen binding protein from *S. aureus* against challenge infection with *S. aureus*. The mice vaccinated with fibrinogen binding proteins showed reduced rates of mastitis compared with controls. Gross examination of challenged mammary glands of mice showed that the glands of mice immunized with fibrinogen binding proteins developed mild intramammary infection or had no pathological changes compared with glands from control mice. A significantly reduced number of bacteria could be recovered in the glands from mice immunized with fibrinogen binding proteins as compared with controls. Mamo then found that vaccination with FnBP-A combined with staphylococcal alpha toxoid did not improve the protection (Mamo, et al., *Vaccine*, 12:988–992, 1994). Next, Mamo, et al., immunized mice with only collagen binding protein, which did not induce protection against the challenge infection with *S. aureus*.

Whole killed staphylococci were included in a vaccine study in humans undergoing peritoneal dialysis (Poole-Warren, et al., *Clinical Nephrology* 35:198–206, 1991). In this clinical trial, a commercially available vaccine of alpha-hemolysin toxoid combined with a suspension of whole killed bacteria) was administered intramuscularly ten times over 12 months, with control patients receiving saline injections. Vaccination elicited significant increases in the levels of antibodies to *S. aureus* cells in the peritoneal fluid and to alpha-hemolysin in the serum. However, immunization did not reduce the incidences of peritonitis, catheter-related infections or nasal colonization among vaccine recipients. The lack of protective efficacy in this trial was attributed to a suboptimal vaccine formulation.

Secreted proteins have been explored as components of subcellular vaccines. The alpha toxin is among the most potent staphylococcal exotoxins; it has cytolytic activity, induces tissue necrosis and kills laboratory animals. Immunization with formaldehyde-detoxified alpha toxin does not protect animals from systemic or localized infections, although it may reduce the clinical severity of the infections (Ekstedt, R. D., *The Staphylococci*, 385–418, 1972)

One study has evaluated the protective efficacy of antibodies to the *S. aureus* microcapsule in an experimental model of staphylococcal infection (Nemeth, J. and Lee, J. C., *Infect. Immun.*, 61:1023–1032, 1993). Rats were actively immunized with killed, microencapsulated bacteria or passively immunized with high-titer rabbit antiserum specific for the capsular polysaccharide. Control animals were injected with saline or passively immunized with normal rabbit serum. Protection against catheter-induced endocarditis resulting from intravenous challenge with the same strain was then evaluated. Despite having elevated levels of anticapsular antibodies, the immunized animals were susceptible to staphylococcal endocarditis and immunized and control animals had similar numbers of bacteria in the blood.

As described in the Detailed Description of the Invention hereinbelow, a number of patents and published patent applications describe the gene sequences for fibronectin, fibrinogen, collagen, elastin, and MHC II antigen type binding proteins. These patents and patent applications are incorporated by reference in their entirety. These documents teach that the proteins, fragments, or antibodies immunoreactive with those proteins or fragments can be used in vaccinations for the treatment of *S. aureus* infections. PCT/US97/087210 discloses the vaccination of mice with a combination of a collagen binding protein (M55 fragment), a fibronectin binding peptide (formalin treated FnBPA (D1–D3)) and a fibrinogen binding peptide (ClfA).

Despite the advances in the art of compositions for the treatment of infections from *Staphylococcus* bacteria such as *S. aureus*, there remains a need to provide a more effective product, and preferably one that exhibits a broad spectrum immunization against a variety of *Staphylococcus* bacterial strains. As described in the Detailed Description of the Invention, one approach to generating a prophylactic immunotherapeutic against bacteria is to stimulate donors with a vaccine containing a combination of MSCRAMMs. This approach of generating hyperimmune globulins can create a steady supply of plasma with high levels of the specific types of disease fighting antibodies. MSCRAMM hyperimmune globulins can be used to provide passive immunity against infection in neonates, trauma patients, immunocompromised patients or patients who are immediately at risk and do not have time to mount their own antibody response. Hyperimmune globulins have a high benefit-to-cost ratio, can be produced from a nonhuman or human source and have a high level of physician acceptance based on past usage.

Therefore, it is an object of the invention to provide new therapeutic compositions for active and passive immunization against *Staphylococcus* infections.

It is another object of the present invention to provide active and passive immunization against mastitis, arthritis, endocarditis, septicemia, osteomyelitis, furunculosis, cellulitis, pyemia, pneumonia, pyoderma, suppuration of wounds, food poisoning, bladder infections and other infectious diseases.

It is another object of the present invention to provide a therapeutic composition that immunizes against *Staphylococcus* bacteria such as *S. aureus* and *S. epidermidis*, increases the rate of opsonization and phagocytosis of a variety of *Staphylococcus* infections, and induces enhanced intracellular killing of *Staphylococcus* bacteria.

It is another object of the present invention to provide an immunological serum against staphylococci.

It is another object of the present invention to provide such a serum which yields humoral and cellular immunity against staphylococci.

It is another object of the present invention to provide such a serum which imparts short-term immunity against staphylococci.

It is a further object of the present invention to provide methods for detecting, diagnosing, treating, preventing or monitoring the progress of therapy for staphylococcal infections.

SUMMARY OF THE INVENTION

A method and composition for the passive immunization of patients infected with or susceptible to infection from *Staphylococcus* bacteria such as *S. aureus* and *S. epidermidis* infection is provided that includes the selection or preparation of a donor plasma pool with high antibody titers to carefully selected *Staphylococcus* adhesins or MSCRAMMs, or fragments or components thereof, or sequences with substantial homology thereto; purification, concentration, and treatment of the donor plasma pool as necessary to obtain immunoglobulin in a purified state that has a higher than normal antibody titer to the selected adhesins; and then administration of an effective amount of the purified immunoglobulin to the patient in need thereof. The donor plasma pool can be prepared, for example, by combining individual blood or blood component samples which have higher than normal titers of antibodies to one or more of the selected adhesins or other proteins that bind to extracellular matrix proteins, or fragments or sequences with substantial homology thereto, to produce the desired composite. Kits for the identification of donor plasma pools with high titers of the selected adhesins are also provided. In an alternative embodiment, a method for obtaining a donor plasma pool that is highly effective against *Staphylococcus* bacterial infection is provided that includes administering carefully selected proteins or peptides to a host to induce the expression of desired antibodies, recovering the enhanced high titer serum or plasma pool from the host, optionally purifying and concentrating the immunoglobulin, and providing it to a patient in need thereof.

A "high titer" of antibody in this context means the presence of an antibody which is immunoreactive with the selected adhesin or fragment thereof which is 2-fold or greater, e.g., up to 10–20 more times higher than that found in a normal population of 100 random samples of blood or blood components.

In one embodiment of the invention, a donor plasma composition is selected or prepared that has a high titer of antibodies to at least a fibrinogen binding protein, such as Clumping factor A ("ClfA") or Clumping factor B ("ClfB"), or fragments or components thereof, or a protein or fragment with sufficiently high homology thereto.

In another embodiment of the invention, a donor plasma composition is selected or prepared that has a high titer of antibodies to at least a collagen binding protein or peptide (or an appropriate site directed mutated sequence thereof), a fragment or component thereof, such as the collagen binding domain protein M55, or a protein or fragment with sufficiently high homology thereto.

In another embodiment of the invention, a donor plasma composition is selected or prepared that has a high titer of antibodies to at least a fibronectin binding protein or peptide (or an appropriate site directed mutated sequence thereof), or a protein or fragment with sufficiently high homology thereto, as well as the fibrinogen binding protein A and B (ClfA or ClfB), or useful fragments or components thereof or a protein or fragment with sufficiently high homology thereto.

In a further embodiment, a donor pool is selected or prepared that has a high titer of antibodies to at least the fibrinogen binding protein A (ClfA) and the fibrinogen binding protein B (ClfB), or useful fragments thereof or a protein or fragment with sufficiently high homology thereto.

In a still further embodiment, a donor pool is selected or prepared with a high titer of antibodies to at least a fibronectin binding protein or peptide (or an appropriate site directed mutated sequence thereof), or a protein or fragment with sufficiently high homology thereto, in combination with (I) high titer antibodies to the fibrinogen binding protein A and B (ClfA and ClfB), or a useful fragment thereof or a protein or fragment with sufficiently high homology thereto; and (ii) high titer antibodies to a collagen binding protein or useful fragment thereof.

In another embodiment, a donor pool is selected or prepared that has a high titer of antibodies as in any of the previous embodiments in combination with a high titer of antibodies to an elastin binding protein or peptide or a protein or fragment with sufficiently high homology thereto.

In another embodiment, a donor pool is selected or prepared that has a high titer of antibodies as set forth in the embodiments above in combination with high titers of antibodies to a MHC II analogous protein or peptide or a protein or fragment with sufficiently high homology thereto.

In an additional embodiment, a donor pool is selected or prepared that has a high titer of antibodies to any of the embodiments above in combination with high titer of antibodies to one or more fibrinogen binding proteins SdrC, SdrD or SdrE, or useful fragments thereof or proteins or fragments with sufficiently high homology thereto.

In still another embodiment, a donor pool is selected or prepared that has a high titer of antibodies to at least the fibrinogen binding protein SdrC, the fibrinogen binding protein SdrD and the fibrinogen binding protein SdrE or useful fragments thereof or a protein or fragment with sufficiently high homology thereto.

Kits are also provided that identify plasma pools with high titers of the desired antibodies. In one embodiment, a suitable amount of antibodies to antibodies of the combination of proteins or peptides as described herein can be immobilized on a solid support and are preferably labeled with a detectable agent. Antibodies can be immobilized to a variety of solid substrates by known methods. Suitable solid support substrates include materials having a membrane or coating supported by or attached to sticks, beads, cups, flat packs, or other solid support. Other solid substrates include cell culture plates, ELISA plates, tubes, and polymeric membranes. The antibodies can be labeled with a detectable agent such as a fluorochrome, a radioactive label, biotin, or another enzyme, such as horseradish peroxidase, alkaline phosphatase and 2-galactosidase. If the detectable agent is an enzyme, a means for detecting the detectable agent can be supplied with the kit. A preferred means for detecting a detectable agent employs an enzyme as a detectable agent and an enzyme substrate that changes color upon contact with the enzyme. The kit can also contain a means to evaluate the product of the assay, for example, a color chart, or numerical reference chart.

Preferably, the isolated immunoglobulin is of the IgG fraction or isotype, but isolated immunoglobulin is not restricted to any particular fraction or isotype and may be IgG, IgM, IgA, IgD, IgE, or any combination thereof. It is also preferable that the isolated immunoglobulin be purely or antigenically human immunoglobulin, which may be obtained from human sources or made directly by the fusion of human antibody producing cells with human antibody producing cells or by the substitution of human DNA sequences for some of the nonhuman DNA sequences which code for the antibody while retaining the antigen binding ability of the original antibody molecule.

BRIEF DESCRIPTION OF THE DRAWING FIGURES

FIG. 1 is a schematic representation of the peptides used in illustrative vaccine, MSCRAMM IV. This drawing illustrates the essential features of the collagen binding MSCRAMM CNA, fibrinogen binding MSCRAMM ClfA, fibrinogen binding MSCRAMM ClfB and fibronectin binding MSCRAMM FnBPA proteins.

Figure 2:
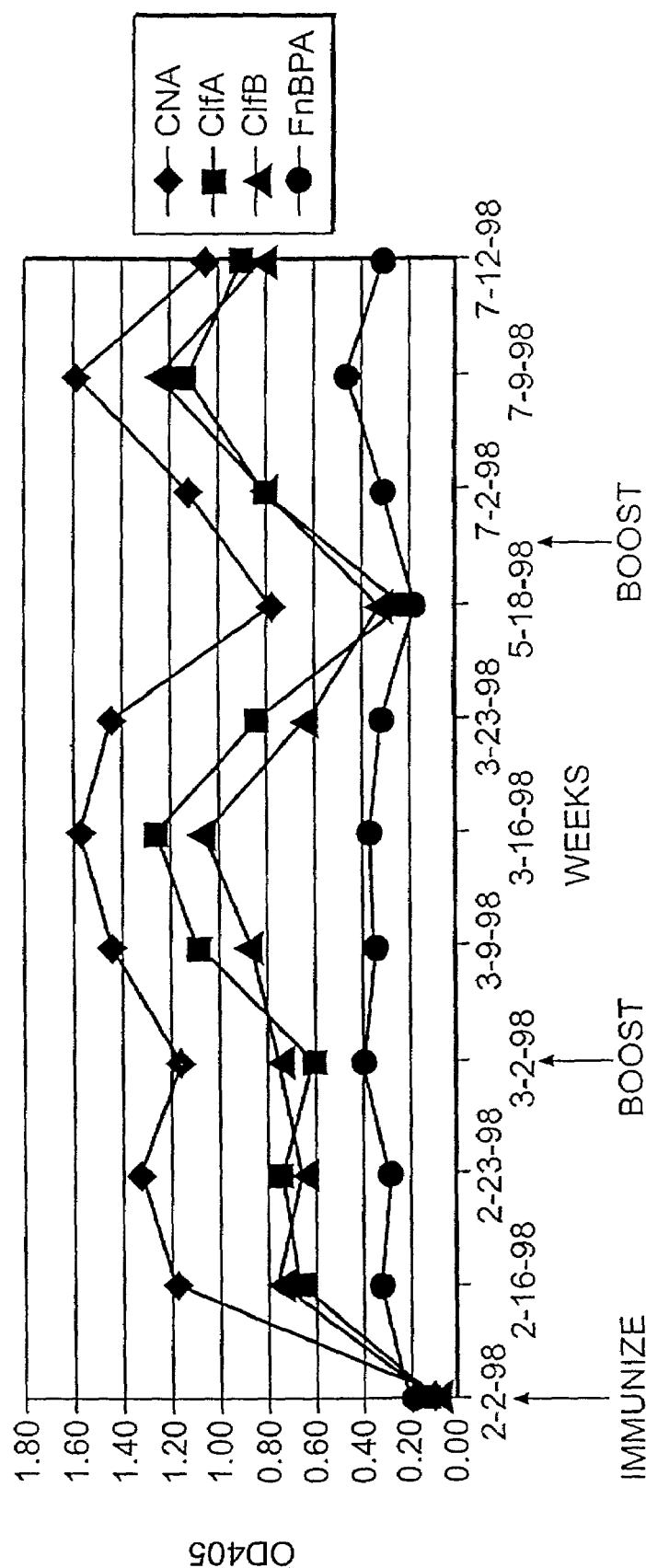

FIG. 2 is a time course graph of the immune response in MCSCRAMM vaccinated Rhesus Monkeys as shown by changes in antibody titers against the MSCRAMMs CNA, ClfA, ClfB and FnBPA, respectively. The titers were analyzed by ELISA and measured as changes in absorbance (quantified at 405 nm) during each week over the course of a six-month period of treatment following the original immunization with the antigen.

DETAILED DESCRIPTION OF THE INVENTION

A method and composition for the passive immunization of patients infected with or susceptible to *Staphylococcus* bacterial infection, such as those caused by *S. aureus* or *S. epidermidis*, is provided that includes the selection or preparation of a donor plasma pool with high antibody titers to carefully selected *Staphylococcus* adhesins, or fragments thereof or sequences with substantial homology thereto; purification, concentration, and treatment of the donor plasma pool as necessary to obtain immunoglobulin in a purified state that has a higher than normal antibody titer to the selected staphylococcal adhesins; and then administration of an effective amount of the purified immunoglobulin to the patient in need thereof. The donor plasma pool can be prepared, for example by, by combining individual blood samples which have higher than normal titers of antibodies to one or more of the selected adhesins or fragments or sequences with substantial homology thereto. Kits for the identification of donor plasma pools with high titers of the selected adhesins are also provided. In an alternative embodiment, a method for obtaining a donor plasma pool that is highly effective against *Staphylococcus* infection is provided that includes administering carefully selected proteins or peptides to a host to induce the expression of desired antibodies, recovering the enhanced high titer plasma pool from the host, optionally purifying and concentrating the immunoglobulin, and providing it to a patient in need thereof.

Donor plasma pools are selected or prepared, purified, treated, and then administered in an effective amount to a patient in need thereof, which include high titer antibodies to at least:

(i) a fibrinogen binding protein, such as Clumping factor A ("ClfA") or Clumping factor B ("ClfB"), or fragments or components thereof, or a protein or fragment with sufficiently high homology thereto;

(ii) a collagen binding protein or peptide (or an appropriate site directed mutated sequence thereof), a fragment or component thereof, such as the collagen binding domain protein M55, or a protein or fragment with sufficiently high homology thereto.

(iii) a fibronectin binding protein or peptide (or an appropriate site directed mutated sequence thereof), or a protein or fragment with sufficiently high homology thereto, in combination with the fibrinogen binding protein A and B (ClfA and ClfB), or useful fragments thereof or a protein or fragment with sufficiently high homology thereto;

(iv) the fibrinogen binding protein A (ClfA) and the fibrinogen binding protein B (ClfB), or useful fragments thereof or a protein or fragment with sufficiently high homology thereto;

(v) fibronectin binding protein or peptide (or an appropriate site directed mutated sequence thereof), or a protein or fragment with sufficiently high homology thereto, in combination with (I) the fibrinogen binding protein A and B (ClfA and ClfB), or a useful fragment thereof or a protein or fragment with sufficiently high homology thereto; and (ii) a collagen binding protein or useful fragment thereof, (vi) components of any of the above in combination with an elastin binding protein or peptide or a protein or fragment with sufficiently high homology thereto;

(vii) components of any of the above embodiments in combination with a MHC II type binding protein or peptide or a protein or fragment with sufficiently high homology thereto;

(viii) components of any of the above embodiments in combination with a the fibrinogen binding proteins SdrC, SdrD or SdrE, or useful fragments thereof or proteins or fragments with sufficiently high homology thereto;

(ix) the fibrinogen binding protein SdrC, the fibrinogen binding protein SdrD and the fibrinogen binding protein SdrE or useful fragments thereof or a protein or fragment with sufficiently high homology thereto; or (x) proteins SdrF, SdrG and SdrH from coagulase-negative bacteria such as *S. epidermidis* or useful fragments thereof or a proteins or fragments with sufficiently high homology thereto.

Isolated peptide fragments from wild-type or naturally occurring variants and synthetic or recombinant peptides corresponding to wild-type, naturally occurring variants or introduced mutations that do not correspond to a naturally occurring binding domain of a binding protein can be used to select or produce donor plasma pools.

I. Definitions

The terms FnBP-A protein, FnBP-B protein, ClfA protein, ClfB protein, SdrC protein, SdrD protein, SdrE protein, CNA protein, EbpS protein and MHCII protein are defined herein to include FNBP-A, FNBP-B, ClfA, ClfB, SdrC, SdrD, SdrE, CNA, EbpS and MHCII subdomains, respectively, and active or antigenic fragments or components of FnBP-A, FnBP-B, ClFA, ClfB, SdrC, SdrD, SdrE, CNA, EbpS and MHCII proteins, respectively, or proteins or fragments having sufficiently high homology thereto. Active fragments or components of FnBP-A, FNBP-B, ClfA, ClfB, SdrC, SdrD, SdrE, CNA, EbpS and MHCII proteins are defined herein as peptides or polypeptides capable of blocking the binding of staphylococci bacteria to extracellular matrix proteins of the host. Antigenic fragments of FnBP-A, FnBP-B, ClfA, ClfB, SdrC, SdrD, SdrE, CNA, EbpS and MHCII proteins are defined herein as peptides or polypeptides capable of producing an immunological response.

The term "adhesin" as used herein includes naturally occurring and synthetic or recombinant proteins and peptides which can bind to extracellular matrix proteins and/or mediate adherence to host cells.

The term "amino acid" as used herein includes naturally occurring and synthetic amino acids and includes, but is not limited to, alanine, valine, leucine, isoleucine, proline, phenylalanine, tryptophan, methionine, glycine, serine, threonine, cysteine, tyrosine, asparagine, glutamate, aspartic acid, glutamic acid, lysine, arginine, and histidine.

An "antibody" is any immunoglobulin, including antibodies and fragments thereof, that binds a specific epitope. The term as used herein includes monoclonal antibodies, polyclonal, chimeric, single chain, bispecific, simianized, and humanized-antibodies as well as Fab fragments, including the products of an Fab immunoglobulin expression library.

The phrase "antibody molecule" in its various grammatical forms as used herein contemplates both an intact immunoglobulin molecule and an immunologically active portion of an immunoglobulin molecule.

As used herein, "pg" means picogram, "ng" means nanogram, "ug" or "µg " mean microgram, "mg" means milligram, "ul" or "µl" mean microliter, "ml" means milliliter, "l" means liter.

A "cell line" is a clone of a primary cell that is capable of stable growth in vitro for many generations.

A "clone" is a population of cells derived from a single cell or common ancestor by mitosis.

A DNA "coding sequence" is a double-stranded DNA sequence which is transcribed and translated into a polypeptide in vivo when placed under the control of appropriate regulatory sequences. The boundaries of the sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genetic DNA sequences from eukaryotic (e.g., mammalian) DNA, and even synthetic DNA sequences. A polyadenylation signal and transcription termination sequence will usually be located 3' to the coding sequence.

"DNA molecule" refers to the polymeric form of deoxyribonucleotides (adenine, guanine, thymine, or cytosine) in its either single stranded form, or a double stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA As used herein, the term "extracellular matrix proteins," or ECM, refers to four general families of macromolecules—collagens, structural glycoproteins, proteoglycans and elastins—that provide support and modulate cellular behavior.

"Immunologically effective amounts" are those amounts capable of stimulating a B cell and/or T cell response.

As used herein, the term "in vivo vaccine" refers to immunization of animals with proteins so as to elicit a humoral and cellular response that protects against later exposure to the pathogen.

The term "ligand" is used to include molecules, including those within host tissues, to which pathogenic bacteria attach.

The term "MHC II analogous proteins" as used herein refers to cell-surface molecules that are responsible for rapid graft rejections and are required for antigen presentation to T-cells.

The phrase "monoclonal antibody" in its various grammatical forms refers to an antibody having only one species of antibody combining site capable of immunoreacting with a particular antigen.

As used herein, the phrase "pharmaceutically acceptable" refers to molecular entities and compositions that are physiologically tolerable and do not typically produce an unacceptable allergic or similar untoward reaction when administered to a human.

As used herein, a "protective antibody" is an antibody which confers protection against infectious diseases caused by infection with staphylococci, when used to passively immunize an naive animal.

As used herein, a "protective epitope" is an epitope which is recognized by a protective antibody, and/or an epitope which, when used to immunize an animal, elicits an immune response sufficient to prevent or lessens the severity for some period of time, of any one of the disorders which can result from infection with staphylococci.

The term "wound" is used herein to mean that normally covering epithelial cellular layer, and other surface structures have been damaged by mechanical, chemical or other influence.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments.

II. Fibronectin-Binding MSCRAMMs

Fibronectin (Fn) is a 440-kDa glycoprotein found in the ECM and body fluids of animals. The primary biological function of fibronectin appears to be related to its ability to serve as a substrate for the adhesion of cells expressing the appropriate integrins. Several bacterial species have been shown to bind fibronectin specifically and to adhere to a fibronectin-containing substratum. Most *S. aureus* isolates bind Fn, but do so in varying extents, which reflects variations in the number of MSCRAMM molecules expressed on the bacterial cell surface. The interaction between Fn and *S. aureus* is highly specific (Kuusela, P., *Nature*, 276:718–20, 1978). Fn binding is mediated by two surface exposed proteins with molecular weights of 110 kDa, named FnBP-A and FnBP-B. The primary Fn binding site consists of a motif of 35–40 amino acids, repeated three to five times. The genes for these have been cloned and sequenced (Jonsson, K., et al., *Eur. J. Biochem.*, 202:1041–1048, 1991). Potential applications for vaccination with anti-FnBP antibodies include, but are not limited to, bovine mastitis, endocarditis and wound infections.

WO-A-85/05553 discloses bacterial cell surface proteins having fibronectin, fibrinogen, collagen, and or laminin binding ability.

U.S. Pat. Nos. 5,320,951 and 5,571,514 to Hook, et al., discloses the gene sequence of fibronectin binding protein A (fnbA), and biological products and methods based on this sequence.

U.S. Pat. No. 5,175,096 to Hook et al., discloses the gene sequence of fnbB, a hybrid DNA molecule (fnbB) and biological products and methods based on this sequence.

U.S. Pat. No. 5,652,217 discloses an isolated and purified protein having binding activity that is encoded by a hybrid DNA molecule from *S. aureus* of defined sequence.

U.S. Pat. No. 5,440,014 discloses a fibronectin binding peptide within the D3 homology unit of a fibronectin binding protein of *S. aureus* which can be used for vaccination of ruminants against mastitis caused by staphylococcal infections, for treatment of wounds, for blocking protein receptors, for immunization of other animals, or for use in a diagnostic assay.

U.S. Pat. No. 5,189,015 discloses a method for the prophylactic treatment of the colonization of a *S. aureus* bacterial strain having the ability to bind to fibronectin in a mammal that includes administering to the mammal in need of treatment a prophylactically therapeutically active amount of a protein having fibronectin binding properties, to prevent the generation of infections caused by a *S. aureus* bacterial strain having the ability to bind fibronectin, wherein the protein has a molecular weight of 87 kDa to 165 kDa.

U.S. Pat. No. 5,416,021 discloses a fibronectin binding protein encoding DNA from *Streptococcus dysgalactiae*, along with a plasmid that includes DNA encoding for fibronectin binding protein from *S. dysgalactiae* contained in *E. coli*, DNA encoding a fibronectin binding protein from *S. dysgalactiae* and an *E. coli* microorganism transformed by DNA encoding a fibronectin binding protein from *S. dysgalactiae*.

It has been observed that antibodies to wild type fibronectin binding protein do not substantially inhibit the ability of *S. aureus* to bind to fibronectin, and thus do not exhibit a significant therapeutic effect in vivo. PCT/US98/01222 discloses antibodies that block the binding of fibronectin to fibronectin binding proteins. The antibodies were raised against a site-directed mutated sequence of fibronectin binding protein that does not bind to fibronectin. It was identified that there is a rapid complexing of fibronectin with fibronectin binding proteins and fragments in vivo. Peptide epitopes that do not bind to fibronectin, even though based on a fibronectin binding domain of a fibronectin binding protein, do not form a complex with fibronectin in vivo. This allows antibodies to be made against the uncomplexed peptide epitope, which inhibit or block the binding of fibronectin to fibronectin binding proteins.

III. Collagen-Binding MSCRAMMs

Collagen is the major constituent of cartilage. Collagen (Cn) binding proteins are commonly expressed by staphylococcal strains. The Cn binding MSCRAMM of *S. aureus* adheres to cartilage in a process that constitutes an important part of the pathogenic mechanism in staphylococcal infections. (Switalski, et al. *Mol. Micro.* 7(1), 99–107, 1993) Cn binding by staphylococcal bacteria such as *S. aureus* is found to play a role in at least, but not only, arthritis and septicemia. CNA proteins with molecular weights of 133, 110 and 87 kDa (Patti, J., et al., *J. Biol. Chem.*, 267: 4766–4772, 1992) have been identified. Strains expressing CNAs with different molecular weights do not differ in their Cn binding ability (Switalski, L. M., et al., *Mol. Microbiol.*, 7:99–107, 1993).

Staphylococcal strains recovered from the joints of patients diagnosed with septic arthritis or osteomyelitis almost invariably express a CNA, whereas significantly fewer isolates obtained from wound infections express this adhesin. (Switalski, L. M., et al., *Mol. Microbiol.*, 7:99–107, 1993) Similarly, *S. aureus* strains isolated from the bones of patients with osteomyelitis more often have an MSCRAMM recognizing the bone-specific protein, bone sialoprotein (BSP) (Ryden, C., et al, *Lancet*, 11:515–518, 1987). *S. aureus* colonization of the articular cartilage within the joint space appears to be an important factor contributing to the development of septic arthritis.

The cloning, sequencing, and expression of a gene CNA, encoding a *S. aureus* CNA protein has been reported (Patti, J., et al., *J. Biol. Chem.*, 267:4766–4772, 1992). The CNA gene encodes an 133-kDa adhesin that contains structural features characteristic of surface proteins isolated from Gram-positive bacteria.

Recently, the ligand-binding site has been localized within the N-terminal half of the CNA (Patti, J. et al., *Biochemistry*, 32:11428–11435, 1993). By analyzing the Col binding activity of recombinant proteins corresponding to different segments of the MSCRAMM, a 168-amino-acid long protein fragment (corresponding to amino acid residues 151–318) that had appreciable Col binding activity was identified. Short truncations of this protein in the N or C terminus resulted in a loss of ligand binding activity but also resulted in conformational changes in the protein.

PCT WO 92/07002 discloses a hybrid DNA molecule which includes a nucleotide sequence from *S. aureus* coding for a protein or polypeptide having collagen binding activity and a plasmid or phage comprising the nucleotide sequence. Also disclosed are an *E. coli* strain expressing the collagen binding protein, a microorganism transformed by the recombinant DNA, the method for producing a collagen binding protein or polypeptide, and the protein sequence of the collagen binding protein or polypeptide.

Patti et al. (*J of Biol Chem.*, 270, 12005–12011, 1995) disclose a collagen binding epitope in the *S. aureus* adhesin encoded by the CNA gene. In this study, the authors synthesized peptides derived from the sequence of the said protein and used them to produce antibodies. Some of these antibodies inhibit the binding of the protein to collagen.

PCT/US97/08210 discloses that certain identified epitopes of the collagen binding protein (M55, M33, and M17) can be used to generate protective antibodies. The application also discloses the crystal structure of the CNA which provides critical information necessary for identifying compositions which interfere with, or block completely, the binding of Col to CNAs. The ligand-binding site in the *S. aureus* CNA and a 25-amino-acid peptide was characterized that directly inhibits the binding of *S. aureus* to 125 I-labeled type II Col.

IV. Fibrinogen-Binding MSCRAMMs

Fibrin is the major component of blood clots, and fibrinogen/fibrin is one of the major host proteins deposited on implanted biomaterials. Considerable evidence exists to suggest that bacterial adherence to fibrinogen/fibrin is important in the initiation of device-related infection. For example, as shown by Vaudaux et al., *S. aureus* adheres to in vitro plastic that has been coated with fibrinogen in a dose-dependent manner (*J. Infect. Dis.* 160:865–875 (1989)). In addition, in a model that mimics a blood clot or damage to a heart valve, Herrmann et al. demonstrated that *S. aureus* binds avidly via a fibrinogen bridge to platelets adhering to surfaces (*J. Infect. Dis.* 167: 312–322 (1993)). *S. aureus* can adhere directly to fibrinogen in blood clots formed in vitro, and can adhere to cultured endothelial cells via fibrinogen deposited from plasma acting as a bridge (Moreillon et al., *Infect. Immun.* 63:4738–4743 (1995); Cheung et al., *J. Clin. Invest.* 87:2236–2245 (1991)). As shown by Vaudaux et al. and Moreillon et al., mutants defective in the fibrinogen-binding protein clumping factor (ClfA) exhibit reduced adherence to fibrinogen in vitro, to explanted catheters, to blood clots, and to damaged heart valves in the rat model for endocarditis (Vaudaux et al., *Infect. Immun.* 63:585–590 (1995); Moreillon et al., *Infect. Immun.* 63: 4738–4743 (1995)).

An adhesin for fibrinogen, often referred to as "clumping factor," is located on the surface of *S. aureus* cells. The interaction between bacteria and fibrinogen in solution results in the instantaneous clumping of bacterial cells. The binding site on fibrinogen is located in the C-terminus of the gamma chain of the dimeric fibrinogen glycoprotein. The affinity is very high and clumping occurs in low concentrations of fibrinogen. Scientists have recently shown that clumping factor also promotes adherence to solid phase fibrinogen, to blood clots, and to damaged heart valves (McDevitt et al., *Mol. Microbiol.* 11: 237–248 (1994); Vaudaux et al., *Infect. Immun.* 63:585–590 (1995); Moreillon et al., *Infect. Immun.* 63: 4738–4743 (1995)).

Two genes in *S. aureus* have been found that code for two Fg binding proteins, ClfA and ClfB. The gene, clfA, was cloned and sequenced and found to code for a polypeptide of 92 kDa. ClfA binds the gamma chain of fibronectin, and ClfB binds the alpha and beta chains (Eidhin, et al., *Mol Micro*, awaiting publication, 1998). ClfB is a cell wall associated protein with a predicted molecular weight of 88 kDa and an apparent molecular weight of 124 kDa that binds both soluble and immobilized fibrinogen and acts as a clumping factor.

The gene for a clumping factor protein, designated ClfA, has recently been cloned, sequenced and analyzed in detail at the molecular level (McDevitt et al., *Mol. Microbiol.* 11: 237–248 (1994); McDevitt et al., *Mol. Microbiol.* 16:895–907 (1995)). The predicted protein is composed of 933 amino acids. A signal sequence of 39 residues occurs at the N-terminus followed by a 520 residue region (region A), which contains the fibrinogen binding domain. A 308 residue region (region R), composed of 154 repeats of the dipeptide serine-aspartate, follows. The R region sequence is encoded by the 18 basepair repeat GAY TCN GAY TCN GAY AGY in which Y equals pyrimidines and N equals any base. The C-terminus of ClfA has features present in many surface proteins of gram-positive bacteria such as an LPDTG motif, which is responsible for anchoring the protein to the cell wall, a membrane anchor, and positive charged residues at the extreme C-terminus.

The platelet integrin alpha IIbβ3 recognizes the C-terminus of the gamma chain of fibrinogen. This is a crucial event in the initiation of blood clotting during coagulation. ClfA and alpha IIbβ3 appear to recognize precisely the same sites on fibrinogen gamma chain because ClfA can block platelet aggregation, and a peptide corresponding to the C-terminus of the gamma chain (198–411) can block both the integrin and ClfA interacting with fibrinogen (McDevitt et al., *Eur. J. Biochem.* 247:416–424 (1997)). The fibrinogen binding site of alpha IIbβ3 is close to, or overlaps, a Ca2+ binding determinant referred to as an "EF hand". ClfA region A carries several EF hand-like motifs. A concentration of Ca2+ in the range of 3–5 mM blocks these ClfA-fibrinogen interactions and changes the secondary structure of the ClfA protein. Mutations affecting the ClfA EF hand reduce or prevent interactions with fibrinogen. Ca2+ and the fibrinogen gamma chain seem to bind to the same, or to overlapping, sites in ClfA region A.

The alpha chain of the leukocyte integrin, alpha MB2, has an insertion of 200 amino acids (A or I domain) which is responsible for ligand binding activities. A novel metal ion-dependent adhesion site (MIDAS) motif in the I domain is required for ligand binding. Among the ligands recognized is fibrinogen. The binding site on fibrinogen is in the gamma chain (residues 190–202). It was recently reported that *Candida albicans* has a surface protein, alpha Intlp, having properties reminiscent of eukaryotic integrins. The surface protein has amino acid sequence homology with the I domain of Mβ2, including the MIDAS motif. Furthermore, Intlp binds to fibrinogen.

ClfA region A also exhibits some degree of sequence homology with alpha Intlp. Examination of the ClfA region A sequence has revealed a potential MIDAS motif. Mutations in putative cation coordinating residues in the DxSxS portion of the MIDAS motif in ClfA results in a significant reduction in fibrinogen binding. A peptide corresponding to the gamma-chain binding site for alpha Mβ2 (190–202) has been shown by O'Connell et al. to inhibit ClfA-fibrinogen interactions (O'Connell et al., *J. Biol. Chem.*, in press). Thus it appears that ClfA can bind to the gamma-chain of fibrinogen at two separate sites. The ligand binding sites on ClfA are similar to those employed by eukaryotic integrins and involve divalent cation binding EF-hand and MIDAS motifs. Despite the low level of identity between ClfA and ClfB, both proteins bind fibrinogen (on different chains) by a mechanism that is susceptible to inhibition by divalent cations, despite not sharing obvious metal binding motifs.

Other fibrinogen binding proteins are disclosed in co-pending U.S. patent application Ser. No. 09/200,650, incorporated herein by reference. This application discloses isolated fibrinogen binding proteins ClfB, SdrC, SdrD and SdrE as well as antibodies to the proteins and diagnostic kits that include the proteins or the antibodies. Also claimed are a method of preventing a *S. aureus* infection that includes administering to the patient an effective amount of ClfB, SdrC, SdrD, SdrE, or a binding fragment thereof and a method of inducing an immunological response comprising administering to a patient a pharmaceutical composition that includes ClfB, SdrC, SdrD, SdrE, or an active fragment thereof.

ClfB has a predicted molecular weight of approximately 88 kDa and an apparent molecular weight of approximately 124 kDa. ClfB is a cell-wall associated protein and binds both soluble and immobilized fibrinogen. In addition, ClfB binds both the alpha and beta chains of fibrinogen and acts as a clumping factor. The ClfB protein has been demonstrated to be a virulence factor in experimental endocarditis.

The SdrC, SdrD and SdrE proteins are related in primary sequence and structural organization to the ClfA and ClfB proteins and are localized on the cell surface. The SdrC, SdrD and SdrE proteins are cell wall-associated proteins, having a signal sequence at the N-terminus and an LPXTG (SEQ ID NO: 2) motif, hydrophobic domain and positively charged residues at the C-terminus. Each also has an SD repeat containing region R of sufficient length to allow efficient expression of the ligand binding domain region A on the cell surface. With the A region of the SdrC, SdrD and SdrE proteins located on the cell surface, the proteins can interact with proteins in plasma, the extracellular matrix or with molecules on the surface of host cells. They share some limited amino acid sequence similarity with ClfA and GlfB. Additionally, SdrC, SdrD and SdrE also exhibit cation-dependent ligand binding to extracellular matrix proteins. For example, SdrC binds vitronectin and SrdE binds bone sialoprotein (BSP).

It has been discovered that in the A region of SrdC, SrdD, SrdE, ClfA and ClfB there is a highly conserved amino acid sequence that can be used to derive a consensus TYTFT-DYVD (SEQ ID NO: 3) motif. The motif can be used in multicomponent vaccines to impart broad spectrum immunity to bacterial infections, and also can be used to produce monoclonal or polyclonal antibodies that impart broad spectrum passive immunity. In an alternative embodiment, any combination of the variable sequence motif derived from the Sdr and Clf protein families, (T/I) (Y/F) (T/N) (F) (T) (D/N) (Y) (V) (D/N), can be used to impart immunity or produce protective antibodies.

ClfB, SdrC, SdrD and SdrE thus share a common consensus TYTFTDYVD (SEQ ID NO: 3) motif which overlaps the ligand binding/Ca2+ binding region of ClfA. Therefore the proteins interact with fibrinogen and other host components. ClfB, SdrC, SdrD and SdrE subdomains, depending on the protein, include subdomains A and B1–B5. Other information regarding extracellular matrix binding proteins has been disclosed in U.S. application Ser. No. 09/200,650, incorporated herein by reference.

V. Elastin-Binding MSCRAMMs

The primary role of elastin is to confer the property of reversible elasticity to tissues and organs (Rosenbloom, J., et al., *FASEB J.*, 7:1208–1218, 1993). Elastin expression is highest in the lung, skin and blood vessels, but the protein is widely expressed in mammalian hosts for *S. aureus*. *S. aureus* binding to elastin was found to be rapid, reversible, of high affinity and ligand specific. Furthermore, a 25 kDa cell surface elastin binding protein (EbpS) was isolated and proposed to mediate *S. aureus* binding to elastin-rich host ECM. EbpS binds to a region in the N-terminal 30 kDa fragment of elastin.

PCT/US97/03106 discloses the gene sequences for an elastin binding protein. DNA sequence data disclosed indicates that the ebps open reading frame consists of 606 bp, and encodes a novel polypeptide of 202 amino acids. EbpS protein has a predicted molecular mass of 23,345 daltons and pI of 4.9. EbpS was expressed in *E. coli* as a fusion protein with polyhistidine residues attached to the N-terminus. A polyclonal antibody raised against recombinant EbpS interacted specifically with the 25 kDa cell surface EbpS and inhibited staphylococcal elastin binding. Furthermore, recombinant EbpS bound specifically to immobilized elastin and inhibited binding of *Staphylococcus aureus* to elastin. A degradation product of recombinant EbpS lacking the first 59 amino acids of the molecule and a C-terminal fragment of CNBr-cleaved recombinant EbpS, however, did not interact with elastin. These results strongly suggest that EbpS is the cell surface molecule mediating binding of *Staphylococcus aureus* to elastin. The finding that some constructs of recombinant EbpS do not interact with elastin suggests that the elastin binding site in EbpS is contained in the first 59 amino acids of the molecule.

Several independent criteria indicate that EbpS is the surface protein mediating cellular elastin binding. First, rEbpS binds specifically to immobilized elastin and inhibits binding of *S. aureus* cells to elastin in a dose dependent manner. These results establish that EbpS is an elastin binding protein that is functionally active in a soluble form. Second, an antibody raised against rEbpS recognizes a 25 kDa protein expressed on the cell surface of *S. aureus* cells. In addition to the size similarity and antibody reactivity, further evidence that this 25 kDa protein is cell surface EbpS is provided by the experiment showing that binding of the 25 kDa protein to immobilized anti-rEbpS IgG is inhibited in the presence of excess unlabeled rEbpS. Finally, Fab fragments prepared from the anti-rEbpS antibody, but not from its pre-immune control, inhibit binding of *S. aureus* to elastin. This result suggests that the topology of surface EbpS is such that the elastin binding site is accessible to interact with ligands (i.e. elastin and the anti-rEbpS Fab fragment) and not embedded in the cell wall or membrane domains. The composite data demonstrate that EbpS is the cell surface protein responsible for binding *S. aureus* to elastin.

The present and previous findings suggest the existence of a functionally active 40 kDa intracellular precursor form of EbpS that requires processing at the C-terminus prior to surface expression. This notion is based on the following observations: i) there exists an intracellular 40 kDa elastin binding protein that is never detected during cell surface labeling experiments, ii) the 25 kDa EbpS and the 40 kDa elastin binding protein have an identical N-terminal sequence, and iii) a single gene exists for EbpS. Because the size of the ebps open reading frame is not sufficient to encode a 40 kDa protein, at first the inventors disregarded this hypothesis. However, their studies with rEbpS demonstrated that although the actual size of the recombinant protein is 26 kDa, it migrates aberrantly as a 45 kDa protein in SDS-30 PAGE. This finding suggests that full length native EbpS, with a predicted size of 23 kDa, may be migrating in SDS-PAGE as the 40 kDa intracellular precursor, and that the 25 kDa surface form of EbpS is actually a smaller form of the molecule processed at the C-terminus. Although EbpS lacks an N-terminal signal peptide and other known sorting and anchoring signals, this proposed intracellular processing event may explain some questions regarding how EbpS is targeted to the cell surface. In fact, C-terminal signal peptides have been identified in several bacterial proteins (Fath, M. J. and Kolter, R., *Microbiol. Rev.*, 57:995–1017, 1993) and alternative means of anchoring proteins to the cells surface have been reported in gram positive bacteria (Yother, J. and White, J. M., *J. Bacteriol.*, 176:2976–2985, 1994).

Using overlapping EbpS fragments and recombinant constructs, the elastin binding site in EbpS was mapped to the amino terminal domain of the molecule (PCT/US97/03106). Overlapping synthetic peptides spanning amino acids 14–34 were then used to better define the binding domain. Among these, peptides corresponding to residues 14–23 and 18–34 specifically inhibited elastin binding by more than 95%. Common to all active synthetic peptides and proteolytic and recombinant fragments of EbpS is the hexameric sequence $^{18}$Thr-Asn-Ser-His-Gln-Asp$^{23}$. Further evidence that this sequence is important for elastin binding was the loss of activity when Asp$^{23}$ was substituted with Asn in the synthetic peptide corresponding to residues 18–34. However, the synthetic hexamer TNSHQD by itself did not inhibit staphylococcal binding to elastin. These findings indicate that although the presence of the TNSHQD sequence is essential for EbpS activity, flanking amino acids in the N- or C-terminal direction and the carboxyl side chain of Asp$^{23}$ are required for elastin recognition.

VI. MHC II-Analogous Proteins, (Map)

In addition to fibrinogen, fibronectin, collagen and elastin. *S. aureus* strains associate with other adhesive eukaryotic proteins, many of which belong to the family of adhesive matrix proteins, such as vitronectin. (Chatwal, G. S., et al., *Infect. Immun.*, 55:1878–1883, 1987). U.S. Pat. No. 5,648,240, incorporated herein by reference, discloses a DNA segment comprising a gene encoding a *S. aureus* broad spectrum adhesin that has a molecular weight of about 70 kDa. The adhesin is capable of binding fibronectin or vitronectin and includes a MHC II mimicking unit of about 30 amino acids. Further analyses of the binding specificities of this protein reveal that it functionally resembles an MHC II antigen in that it binds synthetic peptides. Thus, in addition to mediating bacterial adhesion to ECM proteins, it may play a role in staphylococcal infections by suppressing the immune system of the host. The patent further claims a recombinant vector that includes the specified DNA sequence, a recombinant host cell transformed with the vector, and DNA which hybridizes with the DNA of specified sequence. Also disclosed is a composition that includes a protein or polypeptide encoded by the specified DNA sequence and a method of inducing an immune response in an animal that includes administering an immunogenic composition that includes the encoded protein or polypeptide. A method of making a MHC II antigen protein analog comprising the steps of inserting the specified DNA sequence in a suitable expression vector and culturing a host cell transformed with the vector under conditions to produce the MHC II antigen protein analog is additionally claimed in the patent.

VII. SDR Proteins from *Staphylococcus epidermidis*

*Staphylococcus epidermidis*, a coagulase-negative bacterium, is a common inhabitant of human skin and a frequent cause of foreign-body infections. Pathogenesis is facilitated by the ability of the organism to first adhere to, and subsequently to form biofilms on, indwelling medical devices such as artificial valves, orthopedic devices, and intravenous and peritoneal dialysis catheters. Device-related infections may jeopardize the success of medical treatment and significantly increase patient mortality. Accordingly, the ability to develop vaccines that can control or prevent outbreaks of *S. epidermidis* infection is of great importance, as is the development of means that can prevent or treat infection from a broad spectrum of bacteria, including both coagulase-positive and coagulase negative bacteria. epidermidis have been designated as SdrF, SdrG and SdrH, and the amino acid sequences of these proteins and their nucleic acid sequences are disclosed in co-pending U.S. patent application of Foster et al. which is based on U.S. provisional application Ser. Nos. 60/098,443 and 60/117,119. All of these applications are incorporated herein by reference.

In accordance with the present invention, the donor selection and donor stimulation methods described herein can also be performed with regard to the SdrF, SdrG or an SdrH protein. In these methods, individuals may be identified and selected who have higher than normal antibody titers to the SdrF, SdrG or an SdrH proteins, and a donor plasma pool can be prepared which will have higher than normal titers to one or more of these proteins. Accordingly, donor plasma can be prepared in accordance with the present invention which will be useful in methods to prevent or treat infection from coagulase-negative staphylococcal infections such as those associated with *S. epidermidis*.

VIII. Proteins and Peptides with Substantial Homology or Equivalent Function to Those Described Herein Donor plasma pools can be screened or stimulated as desired, with full sequence proteins, peptides, protein or peptide fragments, isolated epitopes, fusion proteins, or any alternative which binds to the target ECM, whether in the form of a wild type, a site-directed mutant, or a sequence which is substantially homologous thereto.

When used in conjunction with amino acid sequences, the term "substantially similar" means an amino acid sequence which is not identical to published sequences, but which produces a protein or peptide having the same functionality and activities, either because one amino acid is replaced with another similar amino acid, or because the change (whether it be substitution, deletion or insertion) does not substantially effect the active site of the protein. Two amino acid sequences are "substantially homologous" when at least about 70%, (preferably at least about 80%, and most preferably at least about 90 or 95%) of the amino acids match over the defined length of the sequences.

It should also be understood that each of the MSCRAMM polypeptides of this invention may be part of a larger protein. For example, a ClfA polypeptide of this invention may be fused at its N-terminus or C-terminus to a ClfB polypeptide, or to a non-fibrinogen binding polypeptide or combinations thereof. Polypeptides which may be useful for this purpose include polypeptides derived any of the MSCRAMM proteins, and serotypic variants of any of the above.

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second generation molecule. The amino acid changes may be achieved by changing the codons of the DNA sequence, according to Table 1. In keeping with standard polypeptide nomenclature (*J. Biol. Chem.*, 243: 3552–3559, 1969), abbreviations for amino acid residues are shown in Table I. It should be understood by one skilled in the art that the codons specified in Table 1 are for RNA sequences. The corresponding codons for DNA have a T substituted for U.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties which can stimulate the production of a substantially similar antibody. It is thus contemplated by the inventors that various changes may be made in the peptide sequences of the disclosed compositions, corresponding DNA sequences which encode said peptides or antibodies against said peptides without appreciable loss of the biological utility or activity of the donor plasma pool immunoglobulin that is recovered.

TABLE I

| Amino Acids | | Codons |
|---|---|---|
| Alanine | Ala | A GCA GCC GCG GCU |
| Cysteine | Cys | C UGC UGU |
| Aspartic acid | Asp | D GAC GAU GAC GAU |
| Glutamic acid | Glu | F GAA GAG |
| Phenylalanine | Phe | F UUC UUU |
| Glycine | Gly | G GGA GCG GGG GGU |
| Histidine | His | H CAC CAU |
| Isoleucine | Ile | I AUA AUC AUU |
| Lysine | Lys | K AAA AAG |
| Leucine | Leu | L UUA UUG CUA CUC CUG GUU |
| Methionine | Met | M AUG |
| Asparagine | Asn | N AAC AAU |
| Proline | Pro | P CCA CCC CCG CCU |

TABLE I-continued

| Amino Acids | | Codons |
|---|---|---|
| Glutamine | Gln | Q CAA CAG |
| Arginine | Arg | R AGA AGG CGA CGC CGG CGU |
| Serine | Ser | S AGC AGU UCA UCC UCG UCU |
| Threonine | Thr | T ACA ACC ACG ACU |
| Valine | Val | V GUA GUC GUG GUU |
| Tryptophan | Trp | W UGG |
| Tyrosine | Tyr | Y UAC UAU |

It is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+1.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The following non-classical amino acids may be incorporated in the peptide in order to introduce particular conformational motifs: 1,2,3,4-tetrahydroisoquinoline-3—carboxylate (Kazmierski et al., *J. Am. Chem. Soc.*, 113: 2275–2283, 1991); (2S,3S)-methyl-phenylalanine, (2S,3R)-methyl-phenylalanine, (2R,3S)-methyl-phenylalanine and (2R,3R)-methyl-phenylalanine (Kazmierski and Hruby, *Tetrahedron Lett.*, 1991); 2-aminotetrahydronaphthalene-2-carboxylic acid (Landis, Ph.D. Thesis, *University of Arizona*, 1989); hydroxy-1,2,3,4-tetrahydroisoquinoline-3-carboxylate (Miyake et al, *J. Takeda Res. Labs.*, 43:53–76, 1989); β-carboline (D and L) (Kazmierski, Ph.D. Thesis, *University of Arizona*, 1988); HIC (histidine isoquinoline carboxylic acid) (Zechel et al, Int. *J. Pep. Protein Res.*, 43, 1991); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., *J. Org. Chem.*, 50:5834–5838, 1985); β-sheet inducing analogs (Kemp et al., *Tetrahedron Lett.*, 29:5081–5082, 1988); β-turn inducing analogs (Kemp et al., *Tetrahedron Lett.*, 29:5057–5060, 1988); alpha-helix inducing analogs (Kemp et al., *Tetrahedron Lett.*, 29:4935–4938, 1988); ?-turn inducing analogs (Kemp et al., *J. Org. Chem.*, 54:109:115, 1989); and analogs provided by the following references: Nagai and Sato, *Tetrahedron Lett.*, 26:647–650 (1985); DiMaio et al., J. Chem. Soc. *Perkin Trans.*, p. 1687 (1989); also a Gly-Ala turn analog (Kahn et al., *Tetrahedron Lett.*, 30:2317. 1989); amide bond isostere (Jones et al., *Tetrahedron Lett.*, 29:3853–3856, 1988); tetrazol (Zabrocki et al., *J. Am. Chem. Soc.*, 110:5875–5880, 1988); DTC (Samanen et al., *Int. J. Protein Pep. Res.*, 35:501:509, 1990); and analogs taught in Olson et al., *J. Am. Chem. Sci.*, 112:323–333 (1990) and Garvey et al., *J. Org Chem.*, 56:436 (1990). Conformationally restricted mimetics of beta turns and beta bulges, and peptides containing them, are described in U.S. Pat. No. 5,440,013, issued Aug. 8, 1995 to Kahn.

IX. Preparation of Purified Immunoglobulin

In one embodiment, purified immunoglobulin (A,D, E, or G) is prepared that has a high titer of antibodies to the selected adhesins. The term "high titer" in this context means the presence of an antibody in an amount which is 2-fold or greater, e.g., up to 10–20 more times higher than that found in a normal population of 100 random samples of blood.

The blood product can be prepared by (i) selection and purification of the immunoglobulin of a donor which has naturally high titers of antibodies to the selected adhesins, (ii) the combination of donor immunoglobulin from several individuals which have a high titer of antibodies to one or more of the selected adhesins, to produce the desired composite profile; or (iii) stimulation of the desired antibodies in one or more donors to form the desired composite antibody profile by exposing the donor to the selected antigens and obtaining blood sample of the exposed donor after sufficient time to produce and accumulate the resulting immunoreactive antibodies. The first two embodiments are referred to as "donor select" programs and the third is referred to as a "donor stimulation" program.

Donor Stimulation

Using the peptide antigens described herein, the present invention also provides methods of stimulating high antibody levels in a donor, which includes administering to an animal, for example a human, a pharmaceutically-acceptable composition comprising an immunologically effective amount of an MSCRAMM-derived peptide composition. The composition can include partially or significantly purified MSCRAMM-derived peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 30 and about 100 amino acids in length will often be preferred. The antigenic proteins or peptides may also be combined with other agents, such as other staphylococcal or streptococcal peptide or nucleic acid compositions, if desired. The composition may also include staphylococcal produced bacterial components such as those discussed above, obtained from natural or recombinant sources, which proteins may be obtainable naturally or either chemically synthesized, or alternatively produced in vitro from recombinant host cells expressing DNA segments encoding such peptides.

Further means contemplated by the inventors for generating an immune response in an animal includes administering to the animal, or human subject, a pharmaceutically-acceptable composition comprising an immunologically effective amount of a nucleic acid composition encoding a peptide epitope, or an immunologically effective amount of an attenuated live organism that includes and expresses such a nucleic acid composition. Antigenic functional equivalents of the proteins and peptides described herein also fall within the scope of the present invention. Antigenically functional equivalents, or epitopic sequences, may be first designed or predicted and then tested, or may simply be directly tested for cross-reactivity.

In the case of preventing bacterial adhesion, the preparation of epitopes which produce antibodies which inhibit the interaction of a specific gene product or proteoglycans which are structurally similar to the specific gene product are particularly desirable.

The identification or design of suitable MSCRAMM epitopes, and/or their functional equivalents, suitable for use in immunoformulations, vaccines, or simply as antigens (e.g., for use in detection protocols), is a relatively straightforward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The amino acid sequence of these "epitopic core sequences" may then be readily incorporated into peptides, either through the application of peptide synthesis or recombinant technology.

Plasmapheresis

The term plasmapheresis describes a technique in which blood is removed from an animal, separated into its cellular and plasma components, the cells are then returned to the animal, and the plasma retained. Large volume plasmapheresis requires the removed plasma to be replaced by a suitable fluid, and when this is done, the technique is often known as plasma exchange. Any components found in plasma can be removed by plasma exchange. Plasma exchange is the method still in use at most blood banks and public donation centers in the United States. Plasma extracted this way for commercial sale is available for use in a preferred embodiment of this invention.

During plasma donation, it is necessary to replace the fluid taken to prevent circulatory collapse. In most circumstances, the osmotic effect of the plasma needs to be replaced. A 5% solution of human albumin obtained from donor blood is a safe and effective replacement. It is standard practice in the medical community to add 2 ml of KCl solution and 2 ml of 10% calcium gluconate solution to the albumin. Most plasma exchange units replace every 2 liters of plasma removed with 1.5 liters of human albumin solution and 0.5 liters of normal saline.

The methods currently in use for plasma separation are centrifugation and filtration. The technique of U.S. Pat. No. 5,548,066 may be used to prepare the donor plasma pool if it is not commercially available, and is incorporated by reference herein. First, a plurality of blood donors are identified. These donors are mature mammals, typically mammals of the same species for which the serum will be employed. Where a specific ailment is to be treated or prevented, such as mastitis in mammals or other diseases caused by staphylococcal bacteria such as *S. aureus*, it is preferred that the donors have been exposed either naturally or through immunization to the causative organism or some antigenic portion thereof. Further, to achieve a consistent serum product, it is preferred that the donor group be relatively large. It is preferred to use human hosts to prepare the donor plasma pools. Once the donors have been identified, blood is drawn from the donors. Since the serum is refined directly from the blood, it is desired to obtain the maximum quantity of blood to thus obtain the maximum quantity of serum. For humans, an established limit of blood is drawn periodically over time.

It is preferred to identify and maintain a consistent donor group by repeated drawing of smaller quantities of blood, for example, drawing of blood once a month from humans. The frequency of the drawing will of course influence the quantity which may be safely drawn. In general, it is desired to draw the maximum amount of blood over the course of time without causing detriment to the health of the donor. This may dictate drawing small amounts with great frequency, or the maximum amount possible at a reduced frequency, depending upon the particular species. The blood volume of the donor may be estimated by standard formulas available from the Center for Disease Control.

The health of the donor is of course a consideration in this process if long-term bleeding is desired. Before donating, the donor will be checked for general good health, and if the donor is in poor health the bleeding may be deferred until the next scheduled date. Beyond this, it is preferred that long-term health records be kept, preferably including more detailed information. In this regard, it is noted that production quantities of the present serum is a good indicator of the health of the donor.

Typically, the serum is separated from the blood of the donor and consists of material from the immune system. In one method, detailed records are kept for the amount of serum produced from the blood as a yield percentage, such as 7 liters of serum from 14 liters of blood provides a yield of 50%. In the preferred method, records of the yield percentage are kept for each donor for each bleeding. These percentages may then be used to determine if the donor should be bled at the next scheduled time. In particular, if the action to be taken is expressed as a function of yield percentages, a guideline may be expressed as follows: yield percentage </=30%, rest; 31–35%, caution; 36–59%, normal; 60–64%, caution; >/=65%, rest. As may be seen, the donor is not bled if the serum yield is above or below the normal range. Such a yield percentage may indicate an underlying ailment. The subject may be bled, possibly in a reduced amount, in the caution ranges, depending upon the donor's history and/or further examination. In this regard, it has been found that a small percentage of individuals consistently produce yield percentages around 60–62%.

The method of blood and plasma collection is generally standard and well to known to those of skill in the art. Any method can be used that achieves the desired results. Once the blood has been collected, it is subjected to procedures for extracting the desired components. A first important step in this process is to permit each vessel of collected blood to sit at room temperature at least until substantial clotting has occurred, usually one hour. During this period the blood moves from body temperature to room temperature, and is exposed to air. This exposure to air permits the fibrinogen to change into fibrin, causing clotting of the blood.

This clotting period is an important aspect of serum retrieval. The clotting provides a rough separation of the cellular material from the liquid. Additionally, while the exact mechanism is not known, it is believed that the clotting period causes white blood cells to die and, for a percentage of such cells, to burst or rupture such that the chemical material, including antibody, therein is released from the cells. It is believed that this material remains within the serum and acts to provide "information" to the immune system of the recipient of the serum. This "information" may help to "program" white blood cells for particular microorganisms, similar to providing them with a memory of the microorganism, such that the white blood cells of the recipient respond quickly, and in a manner similar to a subject which has been vaccinated or is immune.

This period of non-refrigeration also causes a rough filtering of the collected blood. In particular, the clotted blood with the relatively heavy red blood cells will fall toward the bottom of the vessel, while the liquid plasma, immunoglobulins and chemical material will be pushed toward the top. To assist in this process, and a process described below, it is preferred that the collection vessel be tall and thin, having proportions similar to a standard test tube.

The liquid portion obtained at this stage is raw serum which, after being filtered and sterilized, can impart immunity. Further steps are optionally carried out. However, to increase the yield, various other steps prior to filtration are preferred.

A first of these steps, after the collected blood has had sufficient time to clot, is refrigeration to approximately 20–60° C. This refrigeration reduces the temperature of the blood from room temperature to the refrigeration temperature. Such cooling of course prevents growth of bacteria, mold, etc. Additionally, during this cooling the clotted blood settles further, and the clotted blood contracts. This contraction (and possibly the cooling) may cause a further percentage of the white blood cells to rupture. Additionally, the contraction of the clotted blood serves to express from the clot immunoglobulins and chemical materials which have been trapped therein. This refrigeration should last at least until the blood has achieved the refrigeration temperature, and preferably for about 14–18 hours, or overnight.

A second preferred step is physical pressing of the clotted blood. This pressing is believed to cause yet more rupturing of white cells, thus yielding even more of the transfer factor. Additionally, in a manner similar to the cooling contraction, the pressing serves to force immunoglobulins and transfer factor from the clot.

The preferred method of pressing is to insert a sterile weight into the refrigerated vessel of collected blood. For example, a cylinder having a close sliding fit within the vessel and a weight of approximately two pounds. As may be envisioned, the liquid material will flow about the cylinder until the cylinder has come to rest upon the clotted blood settled at the bottom of the vessel. It is preferred that the pressing weight be maintained in place for about 6–24 hours.

It is noted that the pressing can serve as a first active filtration step. The close fit of the weight serves to separate the liquid raw serum above and the solid material below, although a precision fit of the weight in the vessel is not required. Since this may serve as a first, rough, filtration step, it may conveniently be used to determine the quantity of raw serum produced for calculation of the yield percentage. Specifically, noting the height of the column of raw serum and knowing the diameter of the vessel provides the volume of raw serum produced.

At this point the filtering process proper begins. This further processing includes filtration to remove all cellular material. This filtration is achieved in multiple steps. The first filtration step is a gross filtering. This may be achieved simply by pouring the contents of the vessel into a collection vat while holding a screen over the opening in the collection vessel. Where the high-yield steps of refrigeration and pressing have been used, the pressing cylinder still within the vessel may act in conjunction with the screen to filter, and the screen may mainly filter out the cylinder itself. Where these high-yield steps have not been taken, a finer filter screen may be desired. The clotted cells remaining within the vessel are properly disposed of, and the vessel sterilized for later use.

This is a preferred point for combining the serum from different donors. It is noted, however, that samples from multiple donors can be combined at any point subsequent to the initial gross filtration step.

The raw serum may still contain a large amount of cells and cellular debris. As the next filtration step, the reclaimed liquid is then placed into a continuous flow centrifuge. For example, the liquid may be placed in a Sharples AS16NF continuous flow centrifuge, which will operate at approximately 13,000 to 15,000 rpm. The liquid is drawn off during this process while yet more of the cells and cellular debris is removed.

Following the isolation of the plasma, the antibodies are purified away from other cell products. This can be accomplished by a variety of protein isolation procedures, known to those skilled in the art of immunoglobulin purification, such as ion exchange, affinity purification, etc. Means for preparing and characterizing antibodies are well known in the art. For example, serum samples can be passed over protein A or protein G sepharose columns to bind IgG (depending on the isotype). The bound antibodies are then eluted with, e.g. a pH 5.0 citrate buffer. The elute fractions containing the Abs, are dialyzed against an isotonic buffer. Alternatively, the eluate is also passed over an anti-immunoglobulin-sepharose column. The Ab is then eluted with 3.5 M magnesium chloride. Abs purified in this way can then tested for binding activity by, for example, an isotype-specific ELISA and immunofluorescence staining assay of the target cells.

In an alternative embodiment, the liquid is instead subjected to a further filtration step. This further step actually consists of several sub-steps, with the liquid being passed through several filters of progressively finer gauge. In particular, the liquid is passed through at least a 0.65 micron filter, then a 0.2 micron nominal filter, and then through a 0.2 micron absolute filter. By passing the liquid through the 0.2 nominal filter first, most of the bacteria, mold, and fibrin will be removed prior to passing through the 0.2 absolute filter.

At this point the liquid has had essentially all solid cellular material removed. The chemical materials and immunoglobulins, however, remain in the liquid, which is referred to as clarified serum.

The clarified serum can be used (after sterilization described below) as the final serum. However, it is preferred that the clarified serum be concentrated. This concentration reduces the volume and thus reduces the amount of material which must be shipped. Additionally, certain recipients, such as infant mammals, can not accept a large quantity of medication intravenously due to a lack of capacity. As such, concentration permits a full dosage of the serum to be administered. The concentration is preferably performed by repeated ultra-filtration to remove water molecules, as is known in the art. Such filtration has a cut-off filter of between 10,000 and 100,000 mol. wt. During this process, samples of the clarified serum may be taken to determine if the serum has been sufficiently concentrated. It is preferred that the final serum be concentrated to about 2 to 6 times the clarified serum, and most preferably 2 to 4 times.

Determination of the concentration level is made by testing the amount of IgG (or other immunoglobulin) within the serum. An initial test may be made of the clarified serum, and this result compared with the tests made upon the serum during the ultra-filtration process. For example, if the initial test results in the clarified serum having an IgG concentration of 1 g/100 ml, then the concentration process may be stopped when later tests report an IgG concentration of between about 2–6 g/100 ml, and preferably about 3 g/100 ml. The determination of the IgG amount may be made by the radial immunodiffusion test. However, it is preferred that serum protein electrophoresis be performed on the whole serum to obtain an entire gamma globulin result. This is believed to be more accurate, and provides a clear indication of the IgG level. Once the concentration process has been completed the concentrated unsterilized serum is bottled or packaged using standard procedures.

Upon completion of the concentration and packaging process, the result is unsterilized serum. The next step is to sterilize the serum. While this sterilization is effected, it is important that the unsterilized serum not be denatured. To provide sterilization without denaturing, the unsterilized serum is frozen to a hard freeze condition. For the unsterilized serum, this is approximately −29° C. (−21° F.). While still frozen, the material is then subjected to sufficient gamma irradiation that the material is sterilized, but is not denatured. This level may vary among various species, but may be determined without undue experimentation. It is important that the material be sufficiently cold (hard frozen) such that the material remains frozen during the irradiation step, otherwise denaturing will occur. It is for this reason that the material is frozen to the relatively low temperature. If it is found that if the irradiation process is sufficiently short, or refrigeration is provided during irradiation, then a higher temperature (though still below freezing) could be tolerated.

At this point the final serum has been obtained, although it is frozen. The packages of the serum are thus placed in refrigeration and allowed to thaw to the refrigeration temperature, where they are stored until use.

After administration, the serum has been found to provide cellular immunity similar to a vaccine, and can be used with or without the introduction of the virulent. In general, the present serum should provide protection against bacteria for which the donor group has immunity. In humans, a wide variety of vaccination uses are possible, including general vaccination for individuals with impaired immunity, such as is caused by diabetes, and vaccination for individuals preparing to undergo surgery due to the of nosocomial infection. In addition to humans, the inventive serum should also be of utility for many mammals, such as farm and domestic mammals and humans. For cattle, one particular use would be to avoid bovine mastitis, a common ailment which costs the dairy industry millions of dollars per year.

X. Uses for MSCRAMM and Antibody Compositions

The immunotherapeutic product of the present invention is a purified and concentrated extract of plasma, or serum from a purified donor pool. The serum contains antibodies released from the white blood cells in the extracted blood, and possibly other chemical materials present in the extracted blood. This serum is believed to provide information which is "read" by the immune system of the recipient to provide an extended period of immunity, typically on the order of six to eight weeks. Purified donor plasma pools can be used for the treatment of wounds, for blocking protein receptors or for immunization (vaccination).

The plasma pools comprise antibodies which are useful for interfering with the initial physical interaction between a pathogen and mammalian host responsible for infection, such as the adhesion of bacteria, particularly gram positive bacteria, to mammalian extracellular matrix proteins on in-dwelling devices or to extracellular matrix proteins in wounds; to block protein-mediated mammalian cell invasion; to block bacterial adhesion between mammalian extracellular matrix proteins and bacterial proteins that mediate tissue damage; and, to block the normal progression of pathogenesis in infections initiated other than by the implantation of in-dwelling devices or surgical techniques.

In general, both poly- and monoclonal antibodies against MSCRAMM peptides may be used in a variety of embodiments. For example, they may be employed in antibody cloning protocols to obtain cDNAs or genes encoding the peptides discussed herein or related proteins. They may also be used in inhibition studies to analyze the effects of MSCRAMM-derived peptides in cells or animals. Anti-MSCRAMM epitope antibodies will also be useful in immunolocalization studies to analyze the distribution of MSCRAMMs during various cellular events, for example, to determine the cellular or tissue-specific distribution of the MSCRAMM peptides under different physiological conditions. A particularly useful application of such antibodies is in purifying native or recombinant MSCRAMMS, for example, using an antibody affinity column. The operation of all such immunological techniques will be known to those of skill in the art in light of the present disclosure.

Immunological compositions, including vaccine, and other pharmaceutical compositions containing the selected donor pool plasma concentrate are included within the scope of the present invention. The combination of immunoglobulins against binding proteins, or active or antigenic fragments thereof, or fusion proteins thereof, can be formulated and packaged, alone or in combination with other antibodies, using methods and materials known to those skilled in the art for vaccines. The immunological response may be used therapeutically or prophylactically and may provide passive immunity.

XI. Preparation of Proteins and Antibodies

The skilled reader can employ conventional molecular biology, microbiology, and recombinant DNA techniques to prepare the proteins, peptides, and antibody compositions described herein. Such techniques are explained fully in the literature. See, e.g., Sambrook et al, "Molecular Cloning: A Laboratory Manual" (1989); "Current Protocols in Molecular Biology" Volumes I–III (Ausubel, R. @-I ed., 1994); "Cell Biology: A Laboratory Handbook" Volumes I–III (J. E. Celis, ed., 1994); "Current Protocols in Immunology" Volumes I–III([Coligan, J. E., ed., 1994); "Oligonucleotide Synthesis" (M. J. Gait ed. 1984); "Nucleic Acid Hybridization" (B. D. Hames & S. J. Higgins eds., 1985); "Transcription And Translation" (B. D. Hames & S. J. Higgins, eds., 1984); "Animal Cell Culture" (R. I. Freshney, ed, (1986); "Immobilized Cells And Enzymes (IRL Press, 1986); B. Perbal, "A Practical Guide To Molecular Cloning" (1984).

The antibody obtained through this invention may be labeled directly with a detectable label for identification and quantification of staphylococcal bacterial such as *S. aureus*, *S. epidermidis*, etc. Labels for use in immunoassays are generally known to those skilled in the art and include enzymes, radioisotopes, and fluorescent, luminescent and chromogenic substances including colored particles such as colloidal gold and latex beads. Suitable immunoassays include enzyme-linked immunosorbent assays (ELISA).

Alternatively, the antibody can be labeled indirectly by reaction with labeled substances that have an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art. Antibodies to the binding proteins may also be used in production facilities or laboratories to isolate additional quantities of the protein, such as by affinity chromatography.

In another identification embodiment, microliter plates pre-treated with poly-L-lysine are used to bind one of the target cells to each well, the cells are then fixed, e.g. using 1% glutaraldehyde, and the antibodies are tested for their ability to bind to the intact cell. In addition, FACS, immunofluorescence staining, idiotype specific antibodies, antigen binding competition assays, and other methods common in the art of antibody characterization may be used in conjunction with the present invention to identify preferred donors.

Humanized antibodies are antibodies of animal origin that have been modified using genetic engineering techniques to replace constant region and/or variable region framework sequences with human sequences, while retaining the original antigen specificity.

Such antibodies are commonly derived from rodent antibodies with specificity against human antigens. Such antibodies are generally useful for in vivo therapeutic applications. This strategy reduces the host response to the foreign antibody and allows selection of the human effector functions.

The techniques for producing humanized immunoglobulins are well known to those of skill in the art. For example, U.S. Pat. No. 5,693,762 discloses methods for producing, and compositions of, humanized immunoglobulins having one or more complementarily determining regions (CDR's). When combined into an intact antibody, the humanized immunoglobulins are substantially non-immunogenic in humans and retain substantially the same affinity as the donor immunoglobulin to the antigen, such as a protein or other compound containing an epitope. Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference.

XII. Production of High Titer MSCRAMM-Specific IgG from Biological Fluids Via Affinity Purification In accordance with the present invention, it is also possible to utilize modes of affinity isolation and purification in order to produce high titer MSCRAMM-specific immunoglobulins from biological fluids such as blood or plasma. In the preferred modes of this aspect of the invention, recombinant or wild-type/native MSCRAMMs can be covalently coupled to a substrate or resin, such as Sepharose™ or agarose, to form an affinity matrix. The MSCRAMM affinity matrix can be used to selectively isolate antibodies from serum, plasma, or other biological fluids. In the preferred embodiment, the biological fluid is passed over the MSCRAMM affinity matrix, and the matrix is then washed to remove non-specifically bound antibodies. The washed matrix is then subjected to conditions, such as low pH or high salt, so that MSCRAMM specific antibodies remaining on the matrix are eluted. The anti-MSCRAMM titer of the eluted material will be considerably higher than that of the original biological fluid, and the eluted material can then be utilized in the same manner as the other donor-selected or donor-stimulated compositions of the present invention.

XIII. Pharmaceutical Compositions

Pharmaceutical compositions for immunization of donors containing the MSCRAMM proteins, nucleic acid molecules, antibodies, or fragments thereof may be formulated in combination with a pharmaceutical carrier such as saline, dextrose, water, glycerol, ethanol, other therapeutic compounds, and combinations thereof. The formulation should be appropriate for the mode of administration. Suitable methods of administration include, but are not limited to, oral, anal, vaginal, intravenous, intraperitoneal, intramuscular, subcutaneous, intranasal and intradermal administration.

The preferred route is by intravenous administration.

The pharmaceutical composition for treatment of any of the conditions described herein, should comprise, in a pharmaceutically acceptable excipient, an effective amount of immunoglobulin to treat or prevent the target disorder.

Compositions which contain immunoglobulins as active ingredients are well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. The therapeutic donor immunoglobulin pool compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of MSCRAMM binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more intervals by a subsequent injection or other administration. Alternatively, continuous intravenous infusion sufficient to maintain concentrations of ten nanomolar to ten micromolar in the blood are contemplated.

The immunological compositions, such as vaccines, and other pharmaceutical compositions can be used alone or in combination with other blocking agents to protect against human and animal infections caused by staphylococcal bacterial including *S. aureus* and others. In particular, the compositions can be used to protect humans against endocarditis or to protect humans or ruminants against mastitis caused by staphylococcal infections. The vaccine can also be used to protect canine and equine animals against similar staphylococcal infections.

To enhance immunogenicity, the donor plasma pool concentrate proteins may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 daltons, preferably greater than 10,000 daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

In a preferred embodiment, a donor stimulating vaccine is packaged for immunization by parenteral (i.e., intramuscular, intradermal or subcutaneous) administration or nasopharyngeal (i.e., intranasal) administration. The vaccine is most preferably injected intramuscularly into the deltoid muscle. The vaccine is preferably combined with a pharmaceutically acceptable carrier to facilitate administration. The preferred carrier is usually water or a buffered saline, with or without a preservative. The vaccine may be lyophilized for resuspension at the time of administration or in solution.

The carrier to which the protein may be conjugated may also be a polymeric delayed release system. Synthetic polymers are particularly useful in the formulation of a vaccine to effect the controlled release of antigens. For example, the polymerization of methyl methacrylate into spheres having diameters less than one micron has been reported by Kreuter, J., "Microcapsules and Nanoparticles in Medicine and Pharmacology," M. Donbrow, Ed., CRC Press, p. 125–148.

The amount of immunogen composition used in the production of the polyclonal antibodies varies upon the nature of the immunogen, as well as the animal used for immunization. The preferred dose for human administration is from 0.01 mg/kg to 10 mg/kg, preferably approximately 1 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers such as thimerosal (ethyl(2-mercaptobenzoate-S) mercury sodium salt) (Sigma Chemical Company, St. Louis, Mo.) or physiologically acceptable preservatives.

The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the process may continue.

The compositions preferably further comprise an adjuvant. Many adjuvants are known for use in vaccinations in animals and are readily adapted to this composition. At this time, the only adjuvant widely used in humans has been alum (aluminum phosphate or aluminum hydroxide). Saponin and its purified component Quit A, Freund's complete adjuvant and other adjuvants used in research and veterinary applications have toxicities which limit their potential use in human vaccines.

The isolated peptide can be linked to a selected amino acid sequence to make a fusion protein. As a nonlimiting example, a fusion protein can be made that comprises at least a first peptide of a fibronectin binding domain of fibronectin binding protein operatively linked to a selected amino acid sequence, wherein the first peptide does not specifically bind to fibronectin. In preferred aspects, the first peptide is linked to a selected carrier molecule or amino acid sequence, including, but not limited to, keyhole limpet hemocyanin (KLH) and bovine serum albumin (BSA).

One of the important features provided by the donor stimulation embodiment of the present invention is a polyclonal sera that is relatively homogenous with respect to the specificity of the antibodies therein. Typically, polygonal antisera is derived from a variety of different "clones," i.e., B-cells of different lineage. Monoclonal antibodies, by contrast, are defined as coming from antibody-producing cells with a common B-cell ancestor, hence their "mono" clonality.

When peptides are used as antigens to stimulate the production of polyclonal sera, one expects considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to the present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

XIV. Kits

This invention also includes a kit for the identification of blood or plasma with high titers of desired antibodies. The preferred kit contains sufficient antigen to bind substantially all of the antibody in the sample in about ten minutes or less, or sufficient antibody which can target an antibody in the sample that is to be detected. The antigen or antibody in the kit, e.g., any of the MSCRAMMs or their binding domains as described above, is preferably immobilized on a solid support, and can be labeled with a detectable agent such as those described above or commonly known in the art. The kit optionally contains a means for detecting the detectable agent. If the antigen or antibody in the kit is labeled with a fluorochrome or radioactive label, no means for detecting the agent will typically be provided, as the user will be expected to have the appropriate spectrophotometer, scintillation counter, or microscope. If the detectable agent is an enzyme, a means for detecting the detectable agent can be supplied with the kit, and would typically include a substrate for the enzyme in sufficient quantity to detect all of the antigen-antibody complex. One preferred means for detecting a detectable agent is a substrate that is converted by an enzyme into a colored product. A common example is the use of the enzyme horseradish peroxidase with 2,2'-azino-di-[3-ethyl-benzothiazoline sulfonate] (ABTS).

The invention includes a method for detecting biological samples with an elevated titer of antibodies to selected staphylococcal MSCRAMMs. As used herein the term biological sample refers to a sample of tissue or fluid isolated from a host, typically a human, including, but not limited to, plasma or serum. To confirm that a factor within donor plasma is immunologically cross-reactive with one or more epitopes of the disclosed peptides is a straightforward matter. This can be readily determined using specific assays, e.g., of a single proposed epitopic sequence, or using more general screens, e.g., of a pool of randomly generated synthetic peptides or protein fragments. The screening assays may be employed to identify-either equivalent antigens or cross-reactive antibodies. In any event, the principle is the same, i.e., based upon competition for binding sites between antibodies and antigens.

Any test which measures the binding of an antigen to an antibody can be used to evaluate the level of antigen or antibody in the host's biological sample according to the present invention. A number of other such tests are known and commonly used commercially.

Immunocytochemistry and immunohistochemistry are techniques that use antibodies to identify antigens on the surface of cells in solution, or on tissue sections, respectively. Immunocytochemistry is used to quantitate individual cell populations according to surface markers. Immunohistochemistry is used to localize particular cell populations or antigens. These techniques are also used for the identification of autoantibodies, using tissues or cells that contain the presumed autoantigen as substrate. The antibodies are usually identified using enzyme-conjugated antibodies to the original antibody, followed by a chromogen, which deposits an insoluble colored end product on the cell or tissue.

Another common method of evaluation is a radioimmunoassay, in which radiolabeled reagents are used to detect the antigen or antibody. Antibody can be detected using plates sensitized with antigen. The test antibody is applied and detected by the addition of a radiolabeled ligand specific for that antibody. The amount of ligand bound to the plate is proportional to the amount of test antibody. This test can be reversed to test for antigen. Variations of radioimmunoassays are competition RIA, direct binding RIA, capture RIA, sandwich RIA, and immunoradiometric assay (RMA).

Enzyme linked immunoabsorbent assays (ELISA) are a widely used group of techniques for detecting antigen and antibodies. The principles are analogous to those of radioimmunoassays except that an enzyme is conjugated to the detection system rather than a radioactive molecule. Typical enzymes used are peroxidase, alkaline phosphatase and 2-galactosidase. These can be used to generate colored reaction products from colorless substrates. Color density is proportional to the amount of reactant under investigation. These assays are more convenient than RIA, but less sensitive.

The Western blotting (immunoblotting) method is used to characterize unknown proteins. Components of the biological sample are separated by gel electrophoresis. SDS gels separate according to molecular weight and IEF gels separate the samples according to charge characteristics. The separated proteins are transferred to membranes (blotted) and identified by immunocytochemistry.

Less often used but suitable methods of evaluation include the Farr assay (in which radiolabeled ligands bind to and detect specific antibody in solution which are precipitated and quantified), precipitin reactions (in which antibodies and antigens crosslink into large lattices to form insoluble immune complexes; only works if antigen and antibody are present in sufficient amounts, at near equivalence, and when there are enough epitopes available to form a lattice); nephelometry (measures immune complexes formed in solution by their ability to scatter light); immunodiffusion (detects antigens and antibodies in agar gels); counter-current electrophoresis (similar to immunodiffusion, except that an electric current is used to drive the antibody and antigen together; useful for low concentrations of antigen or antibody); single radial immunodiffusion (SRID)(quantitates antigens by allowing them to diffuse outward from a well into an antibody containing gel; technique can be reversed by diffusing unknown antibody solutions into an antigen-containing well); rocket electrophoresis (similar to SRID, except that the test antigen is moved into the gel by an electric field); and immunofluorescence (similar to immunochemistry, except that it used fluorescence rather than enzyme conjugates). The antibody used to contact the sample of body fluid is preferably immobilized onto a solid substrate. The antibody can be immobilized using a variety of means, as described in *Antibodies: A Laboratory Manual*, cited supra. Suitable solid substrates include those having a membrane or coating supported by or attached to sticks, synthetic glass, agarose beads, cups, flat packs, or other solid supports. Other solid substrates include cell culture plates, ELISA plates, tubes, and polymeric membranes.

Means for labeling antibodies with detectable agents are also described in *Antibodies: A Laboratory Manual*. The amount of antigen in the host biological sample can be determined by any means associated with the selected assay. For example, the selected immunoassay can be carried out with known increasing amounts of antigen to produce a standard curve or color chart, and then the amount of test antigen can be determined by comparing the result of the test to the standard curve or chart that correlates the amount of antigen-antibody complex with known amounts of antigen. The amount of antigen determined to be present in the host biological sample can be used to evaluate the patient's condition in a number of ways. First, the level of antigen can be compared to a population norm based on statistical data. Second, the level of antigen can be considered in light of the patient's own history of antigen level.

The kit can optionally contain a lysing agent that lyses cells present in the sample of body fluid. Suitable lysing agents include surfactants such as Tween-80, Nonidet P40, and Triton X-100. Preferably, the lysing agent is immobilized onto the solid support along with the antibody.

The kit can also contain a buffer solution for washing the substrate between steps. The buffer solution is typically a physiological solution such as a phosphate buffer, physiological saline, citrate buffer, or Tris buffer.

The kit can optionally include different concentrations of a preformed antigen to calibrate the assay. The kit can additionally contain a visual or numeric representation of amounts of antigen in a calibrated standard assay for reference purposes. For example, if an assay is used that produces a colored product, a sheet can be included that provides a depiction of increasing intensities associated with differing amounts of antigen.

The kit can optionally include two antibodies in the detection system. The first antibody which is present in small amounts is specific for the antigen being assayed for. The second antibody provided in higher amounts is used to detect the first antibody. For example, a rabbit antibody can be used to detect the LOOH/amine antigen, and then an anti-rabbit IgG antibody can be used to detect the bound rabbit antibody. Goat antibodies and anti-antibodies are also commonly used.

As one nonlimiting example, a kit for the detection of the lipid peroxidation state of a patient is provided that includes a rabbit antibody specific for desired antibody, anti-rabbit IgG antibody in sufficient amounts to detect the bound first antibody, an enzyme conjugated to the second antibody and a substrate for the enzyme which changes color on exposure to the enzyme.

EXAMPLES

The following examples are included to demonstrate preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Prototype Four Component MSCRAMM Vaccine

A series of recombinant proteins, representing domains from the collagen, Fn, and Fbg-binding MSCRAMMs (FIG. 1), were overexpressed in *E. coli* and affinity purified by metal chelating chromatography as previously described (see, e.g., Joh et al., *Biochemistry*. 33 (20):6086–6092, 1994; Patti et al., *J. Biol. Chem.* 270, 12005–12011, 1995; McDevitt et al., *Mol. Micro.* 11 (2):237–248, 1994; Ni Eidhin et al., *Infect. Immun. Submitted*, 1998). Used were the following: amino acids contained in the recombinant collagen-binding MSCRAMM expressed from CNA (M55, such as disclosed in co-pending U.S. patent application Ser. No. 08/856,253, incorporated herein by reference); amino acids contained in the recombinant fibrinogen-binding MSCRAMM expressed from clfA (Region A, such as disclosed in U.S. patent application Ser. No. 08/293,728, incorporated herein by reference); amino acids contained in the recombinant fibrinogen-binding MSCRAMM expressed from clfB (Region A, such as disclosed in U.S. application Ser. No. 09/200,650, incorporated herein by reference); and amino acids contained in the recombinant fibronectin-binding MSCRAMM (DUD4, such as those disclosed in co-pending U.S. application Ser. No. 09/010,317, incorporated herein by reference). The recombinant FN-binding MSCRAMM protein DUD4 was treated with formalin (5% formalin overnight, 4° C.) prior to combining it with the M55, Region A from ClfA and Region A from ClfB.

Example 2

Example of Growing *E. coli* Strains for Production of Recombinant Proteins

Overnight cultures of *E. coli* JM101 or TOP 3 cells (Stratagene) harboring the recombinant plasmids were diluted 1:50 in 1 L of Luria Broth (Gibco BRL) containing 50 mg/mL ampicillin. *E. coli* cells were grown until the culture reached an $OD_{600}$ of 0.5–0.8. Expression of the recombinant proteins was induced by adding IPTG to a final concentration of 0.2 mM. After a three hour induction period, cells were collected by centrifugation, resuspended in 15 mL of Buffer A (5 mM imidazole, 0.5 M NaCl, 20 mM Tris-HCl, pH 7.9) and lysed by passage through a French press twice at 20,000 lb./in². Cell debris was removed by centrifugation at 50,000×g for 10 min and the supernatant was passed through a 0.45 µM filter.

Example 3

Purification of $HIS_6$ Containing Recombinant Proteins Expressed from pQE-30 (Qiagen®; Qiagen Inc. Chatsworth, Calif.) or PV-4 Based Recombinant Plasmids The recombinant proteins were purified by immobilized metal chelate chromatography, using a column of iminodiacetic acid/Sepharose® 6B Fast Flow (Sigma, St. Louis, Mo.) charged with $Ni^{2+}$; (Porath et al. 1975; Hochuli et al. 1988). The $HIS_6$ tagged proteins were purified by immobilized metal chelate affinity chromatography. More specifically, a column containing iminodiacetic acid Sepharose® 6B FF, connected to a FPLC® system (Pharmacia), was charged with 150 mM $Ni^{++}$ and equilibrated with buffer A (5 mM imidazole, 0.5 M NaCl, 20 mM Tris, pH 7.9). After equilibration, the bacterial supernatant was applied to the column and the column was washed with 10 bed volumes of buffer A. Subsequently, the column was eluted with buffer B (200 mM imidazole, 0.5 M NaCl, 20 mM Tris, pH 7.9). The eluate was monitored for protein by the absorbance at 280 nm and peak fractions were analyzed by SDS-PAGE. Endotoxin was removed from the purified recombinant proteins by detergent extraction with 1% Triton X-114 followed by metal chelate affinity chromatography and passage through a polymyxcin B-sepharose column. The level of endotoxin was quantitated using a chromogenic Limulus Amebocyte Lysate (BioWhittaker, Walkersville, Md.) assay.

Example 4

Immunization of Animals with Four Component MSCRAMM Vaccine—MSCRAMM IV

Rhesus Monkeys

100 µg of M55 (1 EU/mg), ClfA (2.5 EU/mg), ClfB (<1.0 EU/mg), and DUD4 (<10 EU/mg) were mixed together to form the MSCRAMM IV vaccine. The cocktail was mixed with TiterMax™ Gold (CytRX, Norcross, Ga.) in a 1:1 ratio. Two female rhesus monkeys, ID#495Z & 664U (~9.4 kg), were vaccinated intramuscularly (IM) in the hind quadricep with 200 µl of the vaccine. Twenty-eight days later the two monkeys were boosted IM with 200 µl of the same vaccine formulation. Two additional female monkeys, ID#215W & 203U (~8.0 kg), were immunized with the MSCRAMM IV that was compounded in a 1:1 ratio with aluminum hydroxide (2% Alhydrogel; Superfos, Denmark). Twenty-eight days later the two monkeys were boosted IM with 200 µl of the same vaccine formulation.

The clinical regimen followed is described below:

| | |
|---|---|
| Day 0 | 15 ml pre-immunization plasma sample, complete blood chemistry |
| Day 1 | Vaccinate IM hind quadricep with 0.2 ml MSCRAMM IV (100 µg), injection site exam, temperature recorded |
| Day 7 | Liver panel, temperature recorded, injection site exam |
| Day 14 | 15 ml plasma sample |
| Day 21 | 15 ml plasma sample |
| Day 28 | Complete blood chemistry, temperature recorded 15 ml plasma sample, boost with IM injection of 0.2 ml MSCRAMM IV (100 µg) |
| Day 30 | Liver panel, temperature recorded, injection site exam |
| Day 35 | Liver panel, temperature recorded, injection site, 15 ml plasma sample |
| Day 42 | 15 ml plasma sample |
| Day 49 | 15 ml plasma sample |
| Day 106 | 15 ml plasma sample |

All 4 animals seroconverted following the initial immunization. Antibody levels >3 times above background could be detected by ELISA 106 days after the primary vaccination. The four animals received another booster immunization in the 21$^{st}$ week of the study. Each animal was given a booster of four subcutaneous injections of 125 µl of the vaccine for a total booster of 600 µl of the vaccine. Antibody levels at least 3 times above background, and as much as 15 times above background, could be detected by ELISA 189 days after the primary vaccination. See FIG. 2. No adverse injection site reactions were detected by direct observation by veterinarians. In addition, liver enzyme profiles, CBC, and hematology profiles were within the normal range for rhesus monkeys.

Example 5

Analysis of Plasma Samples from the Vaccinated Monkeys were Analyzed by ELISA

Immulon-2 microtiter plates (Dynex Technologies, Chantilly, Va.) were coated overnight at 4° C. with 10 µg/ml (50 µl) of the collagen binding MSCRAMM (M55), fibrinogen binding MSCRAMM (clfA; pCF44), fibrinogen binding MSCRAMM (ClfB; Region A), and the fibronectin binding MSCRAMM (DUD4). Fifty microliters of the diluted plasma samples were added to the MSCRAMM coated wells and incubated for 1 hr at room temperature. Wash buffer consisting of PBS containing 0.05% vol/vol Tween-20, a blocking solution of 1% wt/vol BSA, 0.05% Tween-20 in PBS, and antibody dilution buffer consisting of PBS containing 0.1% BSA, 0.05% Tween-20. Incubation with primary and secondary antibodies was for 60 min at 25° C. The secondary antibody was alkaline phosphatase-conjugated goat anti-monkey immunoglobulin G, (Rockland, Gilbertsville, Pa.), diluted 3500-fold in antibody dilution buffer. ELISA plates were developed for 30 min at 37° C. with 1 mg/mlp-nitrophenyl phosphate (Sigma) in 1 M diethanolamine, 0.5 mM $MgCl_2$, pH 9.8, and quantified at 405 nm on a Perkin Elmer HTS 7000 Bio-Assay reader. Each plasma sample was diluted 100-fold in phosphate buffered saline, containing 0.05% Tween 20, 0.1% BSA, pH 7.4. ELISA data are shown in FIG. 2.

Example 6

Inhibition Assays

Methicillin resistant *S. aureus* strain 601 (Smeltzer, M. S., Gene. 196:249–159, 1997) was cultured under constant rotation for 15 h at 37° C. in BHI broth. A 1:100 dilution of the overnight culture was made into BHI and the bacteria were grown at 37° C. until mid exponential phase. The bacteria were harvested by centrifugation, washed three times in sterile PBS, pH 7.4, and then resuspended in a carbonate buffer (50 mM NaHCO$_3$, pH 8.5). The bacteria were mixed with 1 mg/ml FITC (Sigma; F-7250) in 50 mM NaHCO$_3$, pH 8.5 and incubated end-over-end in the dark for 1 hr at 25° C. The FITC labeling reaction was stopped by centrifugation of the bacterial cells and removing the supernatant containing the unreacted FITC. The labeled bacteria were washed three times in PBS to remove unincorporated FITC, resuspended in PBS, adjusted to ~1×10$^8$ cfu/ml and stored at −20° C. in PBS, pH 7.4.

Example 7

Purification of IgG from Immunized Monkeys

IgG was purified from the monkey plasma by affinity chromatography on PROSEP®-A high capacity resin (Bioprocessing Inc., Princeton, N.J.). Briefly, the plasma was thawed and passed through 0.45µ filter. The plasma was applied to a benchtop column containing PROSEP®-A high capacity resin. The unbound material was removed by washing the column extensively with PBS. The IgG was eluted from the column with 0.1 M sodium citrate, pH 3.0. The pH of eluted IgG was immediately neutralized to pH 6.8–7.4 by the addition of 1M Tris, pH 9.0. The IgG was then dialyzed into PBS, pH 7.4, concentrated and filter sterilized. The concentration of the purified IgG was determined by absorbance at 280 nm.

Example 8

Competitive Inhibition ELISA

Costar 96 well black plates were coated overnight at 4° C. or at room temperature for 2 hr with a 10 µg/ml solution of matrix components consisting of bovine collagen, human fibrinogen, and bovine fibronectin in PBS, pH 7.4. The matrix protein coated plates were washed three times with PBS, 0.05% Tween 20 and then blocked with PBS, 1% BSA. The blocked plates were washed three times with PBS, 0.05% Tween 20. A 500 µl aliquot of FITC-labeled S. aureus cells were mixed with an increasing amount of purified monkey IgG in PBS, 0.05% Tween 20, 0.1% BSA. The labeled cells and IgG were mixed on an end-over-end shaker for 1 hr at 25° C. Fifty µl of the labeled cells/IgG mixture was added to each well on the microtiter plate and incubated at 25° C. on a rocker platform. The wells were washed three times with PBS, 0.05% Tween 20. The amount of bacteria bound to the immobilized matrix proteins was determined on a Perkin Elmer HTS 7000 Bio-Assay reader with the excitation filter set at 485 nm and the emission filter set at 535 nm. Data are shown in FIGS. 3–5.

Example 9

Animal Model of Sepsis

Using a mouse model of sepsis (Bremell, T. A., et al., Infect. Immun. 62 (7):2976–2985, 1992) we have demonstrated that passive immunization with IgG purified from rhesus monkeys immunized with the MSCRAMM IV can protect mice against sepsis induced death. Naive male NMRI mice 5–8 weeks old were passively immunized i.p. on day −1 with 20 mg of either purified IgG from rhesus monkeys immunized with MSCRAMM IV (n=12), or IgG from non-immunized rhesus monkeys (n=13). On day 0, the mice were challenged i.v. with 2.4×10$^7$ CFU/mouse S. aureus strain LS-1. Mortality and weight change was monitored over the next 3 days. Three days after the inoculation 3/13 mice (13%) were dead in the control group, compared to 0/12 mice (0%) in the control group. Mortality in control group at day 13 was 53.8% (7/13) compared to only 16.2% (2/12) for the MSCRAMM IV passively immunized group. The control mice exhibited a significant decrease in their body weight compared to MSCRAMM IV IgG passively immunized mice (28.0±2.5% vs 21.3±3.1%; p<0.01).

Example 10

ELISAs

ELISAs were performed in Immulon-II 96-well microtiter plates (Dynex Technologies, Chantilly, Va.), with wash buffer consisting of PBS containing 0.1% vol/vol Tween-80, a blocking solution of 1% wt/vol BSA, 0.1% Tween-80 in PBS, and antibody dilution buffer consisting of PBS containing 0.05% Tween-80. Incubation with primary and secondary antibodies was for 60 min at 25° C. The secondary antibody was alkaline phosphatase-conjugated goat anti-human immunoglobulin G, (Chemicon, Temecula, Calif.), diluted 3000-fold in antibody dilution buffer. ELISA plates were developed for 30 min at 20° C. with 1 mg/ml p-nitrophenyl phosphate (Sigma) in 1 M diethanolamine, 0.5 mM MgCl$_2$, pH 9.8 and quantified on a Molecular Dynamics ELISA plate reader equipped with a 405 nm filter. Each human serum sample was diluted 100-fold in phosphate buffered saline, containing 0.05% Tween 20, 0.1% BSA, pH 7.4. The ELISA plates were coated overnight at 4° C. with 1 µg/ml (100 µl) of the collagen binding MSCRAMM (M55; Patti, J. M., et al., J. Biol. Chem. 270, 12005–12011, 1995), fibrinogen binding MSCRAMM (clfA; pCF44; McDevitt, D., et al., Mol. Micro. 11 (2):237–248, 1994), fibrinogen binding MSCRAMM (clfb; Region A domain; Ní Edhin, D., et al., Infect. Immun. Submitted, 1998) and the fibronectin binding MSCRAMM (DUD4; Joh, H. J., et al., Biochemistry. 33 (20):6086–6092, 1994). One hundred microliters of the diluted serum samples were added to the MSCRAMM coated wells and incubated for 1 hr at room temperature.

100 human plasma donor samples were analyzed using the above-described ELISA protocol. Eight donors were selected as having elevated MSCRAMM antibody titers ("MSCRAMM Selected"). Plasma units that ranged from 700 ml–850 ml, from eight donors were pooled and the IgG purified by affinity chromatography on PROSEP®-A high capacity resin (Bioprocessing Inc., Princeton, N.J.). Briefly, the human plasma was thawed at 4° C. for 24 hours and the units pooled into one batch. The plasma pool was poured through cheesecloth and then filtered through 0.45µ filter. The plasma was applied to a column of PROSEP®-A high capacity resin connected to a preparative scale HPLC (Waters). The unbound material was removed by washing the column extensively with PBS. The IgG was eluted from the column with 0.1 M sodium citrate, pH 3.0. The pH of eluted IgG was immediately neutralized to pH 6.8–7.4 by the addition of 1M Tris, pH 9.0. The IgG was then dialyzed into PBS, concentrated and filter sterilized. The concentration of the purified IgG was determined by absorbance at 280 nm.

Example 11

Animal Model of S. aureus Infection

A rabbit model of infectious endocarditis (Perlman, B. B., and L. S. Freedman, Yale J. Biol. Med. 42:394–410, 1971) was used to evaluate the prophylactic potential of the "MSCRAMM Selected" human IgG. This model has been used over the past decade to investigate the pathogenesis of endocarditis and to test a variety of new antibiotics and vaccines. In this model, 2.5 kg rabbits underwent a transcarotid-transaortic valvular catheterization with an indwelling polyethylene catheter. Eight rabbits were then treated intraperitoneally with 18 ml of the "MSCRAMM Selected" human IgG (28 mg/ml; 504 mg total). Eight control rabbits received 18 ml sterile PBS and ten rabbits received 500 mg of normal human IVIG (Alpha Therapeutics Veniglobulin S; Los Angeles, Calif.) intraperitoneally. Infective endocarditis was produced 18 hours after IgG administration by an intraperitoneal injection of $10^9$ cfu S. aureus strain Reynolds. The animals were followed for 72 hours and blood samples were obtained at 12-hour intervals. After 72 hours, the animals were euthanized and the kidneys and valvular vegetations aseptically removed. The tissue samples were processed for quantitative culture. Rabbits were considered positive for endocarditis if bacteria were recovered from the vegetations, irrespective of the bacterial density. It should be noted that the lowest level of bacterial detection in this model is =2 $\log_{10}$ cfu/g tissue. The number of organisms recovered from the tissue sites (kidney and valvular vegetations) were statistically compared using a two-tailed Student's t-test. P values lower than 0.05 for individual comparisons are considered significant. The results are shown in table 2.

of the ClfA MSCRAMM protein expressed by S. aureus. Plasma was obtained from Serologicals, Inc. (Clarkston, Ga.) and the IgG was purified by Cangene Corp. as a sterile-filtered solution in 10% maltose, 0.03% polysorbate 80. The material was reported by Cangene to contain 47.55 mg/ml IgG by radial immunodiffusion. This material was stored at 4° C., as directed by the manufacturer. On the day of administration, MS502 was diluted to 40 mg/ml with 1×D-PBS in preparation for an IP injection of 0.5 ml.

SA-IVIG MS503, S. aureus Immunoglobulin Intravenous

Human IgG was purified using 12 units of plasma collected from 5 donors that were determined to possess elevated levels of IgG (>5 fold increase in titer compared to normal IVIG) in an ELISA assay specific for the A domain of the CNA MSCRAMM expressed by S. aureus. Plasma was obtained from Serologicals, Inc. (Clarkston, Ga.) and the IgG was purified by Cangene Corp. as a sterile-filtered solution in 10% maltose, 0.03% polysorbate 80. The material was reported by Cangene to contain 45.41 mg/ml IgG by radial immunodiffusion. This material was stored at 4° C., as directed by the manufacturer. On the day of administration, MS503 was diluted to 40 mg/ml with 1×D-PBS in preparation for an IP injection of 0.5 ml.

Control, Human Immune Globulin Intravenous, Polygam® (Baxter IVIG)

A sterile freeze-dried preparation of IgG was manufactured from large pools of human plasma by Baxter Healthcare Corp. The material was reconstituted in sterile water for injection according to the manufacturer's directions (Baxter Healthcare Corp.). The 5% solution contains 50 mg/ml total

TABLE 2

| ANIMAL GROUP | FREQUENCY OF ENDOCARDITIS | FREQUENCY OF RENAL SEEDING | MEAN VEGETATION DENSITIES $\log_{10}$ cfu/g ± SD | MEAN RENAL DENSITIES $\log_{10}$ cfu/g ± SD |
|---|---|---|---|---|
| A | 7/8 | 8/8 | 6.07 ± 3.33 | 4.48 ± 1.32 |
| B | 1/8 | 0/8 | 2.25 ± 0.62* | 2.00 ± 0.00^ |
| C | 10/10 | 10/10 | 7.42 ± 3.45 | 6.17 ± 2.08 |

Group A = PBS
Group B = MSCRAMM selected human IgG
Group C = Normal IVIG (Alpha Therapeutics Veniglobulin S)
*p = 0.05 (vs. group A)
^p = 0.05 (vs. group A), p = 0.001 (vs. group C)

Example 12

Tests Regarding ClfA and CNA Selected Human IVIG

A. Prophylactic Administration of ClfA and CNA Donor Selected SA-IVIG IVIG

The objective of the studies described here was to determine if passive immunization with donor selected IVIG products prepared from human donor plasma containing high titers of antibodies against microbial surface components recognizing adhesive matrix molecule (MSCRAMM) proteins expressed by Staphylococcus aureus (S. aureus) can prevent mortality caused by an antibiotic resistant S. aureus clinical isolate in a murine septicemia model.

SA-IVIG MS502, S. aureus Immunoglobulin Intravenous

Human IgG was purified using 15 units of plasma collected from 7 donors that were determined to possess elevated levels of IgG (>5 fold increase in titer compared to normal IVIG) in an ELISA assay specific for the A domain protein, 45 mg/ml IgG, 8.5 mg/ml NaCl, 3 mg/ml human albumin, 22.5 mg/ml glycine, 20 mg/ml glucose, 2 mg/ml polyethylene glycol, 1 µg/ml tri(n-butyl) phosphate, 1 µg/ml octoxynol 9 and 100 µg/ml polysorbate 80. Prior to injection the stock was diluted in sterile distilled water to a final concentration of 40 mg/ml IgG in preparation for an IP injection of 0.5 ml.

S. aureus

S. aureus strain 601 (Smeltzer, et. al., 1996) was obtained from Dr. M. S. Smeltzer, University of Arkansas for Medical Sciences. This S. aureus strain was isolated from an intensive care unit. The isolate is cephalothin, ciprofloxacin, clindamycin, erythromycin, oxacillin (methicillin), penicillin-G and trimethoprin-sulfamethoxazole resistant. Strain 601 S. aureus cells taken from a frozen glycerol stock, were inoculated into a 10 ml BHI broth culture and grown over night at 37° C. Cells from the overnight culture were diluted 1:100 in BHI broth and grown at 37° C. for approximately 3 hours until the absorbance at 600 nm reached 1.8–2.0 OD units. The bacteria were pelleted by centrifugation and resuspended in ⅕ volume of freezing medium (1×D-PBS, pH 7.4; 10% DMSO; 5% BSA). A small aliquot of the stock was plated on blood agar dishes at $10^{-2}$, $10^{-4}$ and $10^{-6}$ dilutions and cultured over night to determine the CFU concentration of the preparation. The bacterial preparation was stored at −86° C. until used. On the day of injection, the frozen bacterial stock was thawed and pelleted by centrifugation. The bacteria were washed once in D-PBS and resuspended to the appropriate concentration in D-PBS for IV injection. A portion of the bacterial suspension was plated on blood agar dishes at $10^{-2}$, $10^{-4}$ and $10^{-4}$ dilutions and cultured over night to determine the CFU concentration of the final injected preparation.

Animal Sex, Species, Number, Age and Source 56 female mice (5–6 weeks of age) were purchased from Taconic Quality Laboratory Animals and Services for Research (Germantown, N.Y.). Animals were allowed to acclimate for at least 14 days prior to initiation of treatment. Upon arrival, the mice were examined, group housed (5/cage) in polycarbonate shoe box cages with absorbent bedding. All mice were placed on a 12 hour light-dark cycle under the required husbandry standards found in the NIH Guide for the Care and Use of Laboratory Animals.

Identification and Randomization

All animals were uniquely identified using tail tattoos prior to dosing. Prior to initiation of treatment, the animals were individually weighed and their health was evaluated. Mice were randomized and assigned to treatment groups using stratified body weights.

Experimental Design

On Day −1, animals were treated with a single 0.5 ml IP injection of MS502, MS503 or Baxter IVIG. On Day 0, $2.2 \times 10^8$ CFU S. aureus were administered by a single IV injection (0.1 ml) to all animals via the tail vein.

DATA

Mice were pre-treated by intraperitoneal (IP) injection with 20 mg of either Baxter's normal IVIG product or 20 mg SA-IVIG MS502 and 20 mg SA-IVIG MS503. MS502 was an immunoglobulin G (IgG) preparation purified from donor plasma containing elevated titers of antibodies recognizing the A domain of clumping factor (ClfA), a S. aureus fibrinogen binding MSCRAMM protein. Likewise MS503 was a high titer preparation selected for recognition of the A domain of CNA, the collagen binding S. aureus MSCRAMM. The total IgG concentrations of the two MSCRAMM preparations and the standard Baxter's normal product is provided in Table 3, below. As shown below, the high-titer MS502 sample had a total ClfA content of 2.29 Units/mg as opposed to only 0.2 Units/mg in the normal sample. The high-titer MS503 sample had a total CNA content of 1.06 Units/mg as opposed to only 0.2 Units/mg in the normal sample. 24 hours after IgG administration, the mice were challenged with a single intravenous (IV) injection of a methicillin-resistant strain of S. aureus (Strain 601). The mice were followed for 5 days at which point all remaining mice were sacrificed. Significant differences in the relative survival times between treatment groups were detected. Sixty-three percent (12/19) of the mice that received MS502 (p=0.003 vs. control; Mantel-Cox survival analysis) survived the bacterial challenge. Sixty-eight percent (13/19) of the mice that received MS503 (p=0.0008 vs. control; Mantel-Cox survival analysis) survived the bacterial challenge. Only 22% (4/18) of the mice treated with normal human IVIG survived the entire study period. These results clearly indicate that prophylactic administration of ClfA and CNA donor selected SA-IVIG IVIG provides a significant level of protection against lethal infection as compared to a commercially available normal human IVIG product.

TABLE 3

| Product | Selection on MSCRAMM | Total IgG Concentration (mg/ml) | C1fA (Units/mg) | CNA (Units/mg) |
|---|---|---|---|---|
| Normal Donor Pool | Unselected | 45.00 | 0.2 | 0.2 |
| MS502 | C1fA | 47.55 | 2.29 | NT |
| MS503 | CAN | 45.41 | NT | 1.06 |

NT = not tested
Baxter Gammagard ® IgIV represents a normal unselected IgIV

B. Therapeutic Applications of ClfA-selected Human SA-IVIG

SA-IVIG MS502, S. aureus Immunoglobulin Intravenous

Human IgG was purified using 15 units of plasma collected from 7 donors that were determined to possess elevated levels of IgG (>5 fold increase in titer compared to normal IVIG) in an ELISA assay specific for the A domain of the ClfA MSCRAMM protein expressed by S. aureus. Plasma was obtained from Serologicals, Inc. (Clarkston, Ga.) and the IgG was purified by Cangene Corp. as a sterile-filtered solution in 10% maltose, 0.03% polysorbate 80. The material was reported by Cangene to contain 47.55 mg/ml IgG by radial immunodiffusion. This material was stored at 4° C., as directed by the manufacturer. On the day of administration, MS502 was diluted to 40mg/ml with 1×D-PBS in preparation for an IP injection of 0.5 ml.

S. aureus

S. aureus strain 601 (Smeltzer, et. al., 1996) was obtained from Dr. M. S. Smeltzer, University of Arkansas for Medical Sciences. This S. aureus strain was isolated from an intensive care unit. The isolate is cephalothin, ciprofloxacin, clindamycin, erythromycin, oxacillin (methicillin), penicillin-G and trimethoprin-sulfamethoxazole resistant. Strain 601 S. aureus cells taken from a frozen glycerol stock, were inoculated into a 10 ml BHI broth culture and grown over night at 37° C. Cells from the overnight culture were diluted 1:100 in BHI broth and grown at 37° C. for approximately 3 hours until the absorbance at 600 nm reached 1.8–2.0 OD units.

The bacteria were pelleted by centrifugation and resuspended in ⅕ volume of freezing medium (1×D-PBS, pH 7.4; 10% DMSO; 5% BSA). A small aliquot of the stock was plated on blood agar dishes at $10^{-2}$, $10^{-4}$ and $10^{-6}$ dilutions and cultured over night to determine the CFU concentration of the preparation. The bacterial preparation was stored at −86° C. until used. On the day of injection, the frozen bacterial stock was thawed and pelleted by centrifugation. The bacteria were washed once in D-PBS and resuspended to the appropriate concentration in D-PBS for IV injection. A portion of the bacterial suspension was plated on blood agar dishes at $10^{-2}$, $10^{-4}$ and $10^{-6}$ dilutions and cultured over night to determine the CFU concentration of the final injected preparation.

Animal Sex, Species, Number, Age and Source

Female mice (5–6 weeks of age) were purchased from Taconic Quality Laboratory Animals and Services for Research (Germantown, N.Y.). Animals were allowed to acclimate for at least 5 days prior to initiation of treatment. Upon arrival, the mice were examined, group housed (5/cage) in polycarbonate shoe box cages with absorbent bedding. All mice were placed on a 12 hour light-dark cycle under the required husbandry standards found in the NIH Guide for the Care and Use of Laboratory Animals.

Identification and Randomization

All animals were uniquely identified using tail tattoos prior to dosing. Prior to initiation of treatment, the animals were individually weighed and their health was evaluated. Mice were randomized and assigned to treatment groups using stratified body weights.

Experimental Design

On Day −1, animals were treated with a single 0.5 ml IP injection of MS502 IVIG. On Day 0, $5.6 \times 10^7$ CFU *S. aureus* 601 was administered by a single IV injection (0.1 ml) to all animals via the tail vein. In addition, a group of mice received MS502 IVIG 3 hours after the IV bacterial challenge. Control mice were left untreated.

DATA

Mice were treated by intraperitoneal (IP) injection with 20 mg of SA-IVIG MS502 either 18 or prior or 3 hours after an IV challenge with *S. aureus* 601. MS502 was an immunoglobulin G (IgG) preparation purified from donor plasma containing elevated titers of antibodies recognizing the A domain of clumping factor (ClfA), a *S. aureus* fibrinogen binding MSCRAMM protein. The mice were followed for 5 days at which point all remaining mice were sacrificed. Ninety-three percent of the mice that received MS502 SA-IVIG 18 hours prior to *S. aureus* challenge survived. Similarly, 93% of the mice that received MS502 SA-IVIG 3 hours post bacterial challenge survived. In contrast, only 76% of the control mice survived the bacterial challenge. These results clearly indicate that therapeutic administration of ClfA donor selected human SA-IVIG provides a significant and effective treatment of staphylococcal infection as compared to a commercially available normal human IVIG product.

What is claimed is:

1. A method of obtaining a purified human donor immunoglobulin composition comprising an antibody titer to an *S. aureus* serine-aspartate repeat (Sdr) protein in combination with an antibody titer to an *S. epidermidis* serine-asparate repeat (Sdr) protein wherein both antibody titers are higher than that found in pooled intravenous immunoglobulin obtained from unselected human donors, said method comprising obtaining blood or plasma samples from human donors, screening said samples so as to select those samples having an antibody titer to an *S. aureus* Sdr protein and an antibody titer an *S. epidermidis* Sdr protein that are both in an amount that is higher than that found in pooled intravenous immunoglobulin obtained from unselected donors, recovering blood or plasma from the selected high-titer donors, and treating the donor blood plasma to obtain immunoglobulin in a purified state having an antibody titer to an *S. aureus* Sdr protein and an antibody titer to an *S. epidermidis* Sdr protein that are both in an amount which is higher than that found in pooled intravenous immunoglobulin obtained from unselected human donors.

2. The method of claim 1 wherein the *S. aureus* Sdr protein is selected from the group consisting of clumping factor A (ClfA), clumping factor B (ClfB), SdrC, SdrD, and SdrE.

3. The method of claim 1 wherein the *S. epidermidis* Sdr protein is selected from the group consisting of SdrF, SdrG and SdrH.

4. The method of claim 1 wherein the resulting composition has an antibody titer to an *S. aureus* Sdr protein in an amount that is 2-fold or greater than that found in pooled intravenous immunoglobulin obtain from unselected donors.

5. The method of claim 1 wherein the resulting composition has a total antibody titer to an *S. aureus* Sdr protein that is greater than 0.2 Units/mg/lgG.

6. The method according to claim 1 wherein donors having a high titer to a *staphylococcal* Sdr protein are determined by identifying those samples having a high titer of antibodies to the A domain of the *staphylococcal* Sdr protein.

7. A method of obtaining a purified human donor immunoglobulin composition comprising an antibody titer to an *S. aureus* serine-aspartate repeat (Sdr) protein in combination with an antibody titer to an *S. epidermidis* serine-asparate repeat (Sdr) protein wherein both antibody titers are higher than that found in pooled intravenous immunoglobulin obtained from unselected human donors, said method comprising administering an *S. aureus* Sdr protein to a human host donor in an amount sufficient to induce an antibody titer to the *S. aureus* Sdr protein that is higher that found in pooled intravenous immunoglobulin obtained from unselected donors, and administering an *S. epidermidis* Sdr protein to a human host donor in an amount sufficient to induce an antibody titer to the *S. epidermidis* Sdr protein that is higher than that found in pooled intravenous immunoglobulin obtained from unselected donors, recovering blood or plasma samples from the induced donors, and treating the donor blood or plasma to obtain immunoglobulin in a purified state having antibody titer to an *S. aureus* Sdr protein and an antibody titer to an *S. epidermidis* Sdr protein that are both in an amount which is higher than that found in pooled intravenous immunoglobulin obtained from unselected human donors.

8. The method of claim 7 wherein the *S. aureus* Sdr protein is selected from the group consisting of clumping factor A (ClfA), clumping factor B (ClfB), SdrC, SdrD, and SdrE.

9. The method of claim 7 wherein the *S. epidermidis* Sdr protein is selected from the group consisting of SdrF, SdrG and SdrH.

10. The method of claim 7 wherein the resulting composition has an antibody titer to an *S. aureus* Sdr protein in an amount that is 2-fold or greater than that found in pooled intravenous immunoglobulin obtain from unselected donors.

11. The method of claim 7 wherein the resulting composition has a total antibody titer to an *S. aureus* Sdr protein that is greater than 0.2 Units/mg/lgG.

12. The method of claim 7 wherein the Sdr protein administered to a human host donor is the A domain of the staphylococcal Sdr protein.

* * * * *

UNITED STATES PATENT AND TRADEMARK OFFICE
CERTIFICATE OF CORRECTION

PATENT NO.      : 7,045,131 B2                                    Page 1 of 1
APPLICATION NO. : 10/091494
DATED           : May 16, 2006
INVENTOR(S)     : Patti et al.

It is certified that error appears in the above-identified patent and that said Letters Patent is hereby corrected as shown below:

On the title page: (73) Assignee: change "Inhibitex, Inc., Alpharetta, GA (US)" to --Inhibitex, Inc., Alpharetta, GA (US); The Provost Fellows and Scholars of the College of the Holy and Undivided Trinity of Queen Elizabeth Near Dublin, Dublin (IRELAND); The Texas A&M University System, College Station, TX (US) --.

Signed and Sealed this

First Day of May, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 18
<212> TYPE: DNA
<213> ORGANISM: Staphylococcus aureus
<220> FEATURE:
<221> NAME/KEY: MISC_FEATURE
<222> LOCATION: (6) and (12)
<223> OTHER INFORMATION: n = (a or c or g or t)

<400> SEQUENCE: 1
gaytcngayt cngayagy                                                   18

<210> SEQ ID NO 2
<211> LENGTH: 5
<212> TYPE: PRT
<213> ORGANISM: Staphylococcus aureus
<220> FEATURE:
<221> NAME/KEY: MISC_FEATURE
<222> LOCATION: (3)..(3)
<223> OTHER INFORMATION: Xaa can be any amino acid

<400> SEQUENCE: 2

Leu Pro Xaa Thr Gly
1               5

<210> SEQ ID NO 3
<211> LENGTH: 9
<212> TYPE: PRT
<213> ORGANISM: Staphylococcus aureus

<400> SEQUENCE: 3

Thr Tyr Thr Phe Thr Asp Tyr Val Asp
1               5

<210> SEQ ID NO 4
<211> LENGTH: 6
<212> TYPE: PRT
<213> ORGANISM: Staphylococcus aureus

<400> SEQUENCE: 4

Thr Asn Ser His Gln Asp
1               5